United States Patent
Hoskins et al.

(10) Patent No.: US 12,110,531 B2
(45) Date of Patent: Oct. 8, 2024

(54) METHOD FOR INCREASING OIL YIELD DURING ETHANOL PRODUCTION

(71) Applicant: DANSTAR FERMENT AG, Zug (CH)

(72) Inventors: Brian Hoskins, San Diego, CA (US);
Anthony V. Newton, San Diego, CA (US); Yun Han, San Diego, CA (US);
Joseph P. Borst, Wyandotte, MI (US)

(73) Assignee: DANSTAR FERMENT AG, Zug (CH)

( * ) Notice: Subject to any disclaimer, the term of this patent is extended or adjusted under 35 U.S.C. 154(b) by 893 days.

(21) Appl. No.: 16/621,957

(22) PCT Filed: Jun. 14, 2018

(86) PCT No.: PCT/US2018/037614
§ 371 (c)(1),
(2) Date: Dec. 12, 2019

(87) PCT Pub. No.: WO2018/232165
PCT Pub. Date: Dec. 20, 2018

(65) Prior Publication Data
US 2023/0159965 A1 May 25, 2023

Related U.S. Application Data

(60) Provisional application No. 62/520,998, filed on Jun. 16, 2017.

(51) Int. Cl.
*C12P 7/64* (2022.01)
*C12N 9/26* (2006.01)
*C12P 7/06* (2006.01)

(52) U.S. Cl.
CPC .............. *C12P 7/64* (2013.01); *C12N 9/2414* (2013.01); *C12P 7/06* (2013.01); *C12Y 302/01001* (2013.01)

(58) Field of Classification Search
CPC .............. C12P 7/64; C12P 7/06; C12N 9/2414
See application file for complete search history.

(56) References Cited

U.S. PATENT DOCUMENTS

| | | | |
|---|---|---|---|
| 5,489,530 A | 2/1996 | Braatz et al. | |
| 7,314,739 B2 | 1/2008 | Matuschek et al. | |
| 2003/0013172 A1* | 1/2003 | Gerendash | C12N 9/2417 435/189 |
| 2011/0039308 A1* | 2/2011 | Slupska | C12N 9/2414 435/157 |
| 2012/0171731 A1 | 7/2012 | Nedwin et al. | |
| 2014/0073036 A1* | 3/2014 | Hunt, Jr. | C11D 3/38663 510/393 |
| 2016/0017305 A1 | 1/2016 | Cascao-Pereira et al. | |
| 2016/0152922 A1 | 6/2016 | Kreel et al. | |
| 2016/0264951 A1 | 9/2016 | Callen et al. | |

FOREIGN PATENT DOCUMENTS

| | | |
|---|---|---|
| WO | 1993/000924 | 1/1993 |
| WO | 1994/019454 | 9/1994 |
| WO | 1997/44361 | 11/1997 |
| WO | 2002/068589 | 9/2002 |
| WO | 2002/092802 | 11/2002 |
| WO | 2003/018766 | 3/2003 |
| WO | 2003/035878 | 5/2003 |
| WO | 2003/083054 | 10/2003 |
| WO | 2003/089620 | 10/2003 |
| WO | 2004/091544 | 10/2004 |
| WO | 2005/032496 | 4/2005 |
| WO | 2005/086900 | 9/2005 |
| WO | 2006/031699 | 3/2006 |
| WO | 2008/036863 | 3/2008 |
| WO | 2008/080093 A2 | 7/2008 |
| WO | 2009/020459 | 2/2009 |
| WO | 2010/008841 | 1/2010 |
| WO | 2010/074999 | 7/2010 |
| WO | 2011/017093 | 2/2011 |
| WO | 2011/046812 | 4/2011 |
| WO | 2011/080352 | 7/2011 |
| WO | 2011/080354 | 7/2011 |
| WO | 2011/082429 | 7/2011 |
| WO | 2013/116175 | 8/2013 |
| WO | 2013/148163 | 10/2013 |
| WO | 2014/007921 | 1/2014 |
| WO | WO-2017/059083 A1 | 4/2017 |
| WO | WO-2017/106633 A1 | 6/2017 |
| WO | 2020/068597 | 4/2020 |

OTHER PUBLICATIONS

Extended European Search Report from corresponding European Patent Appln. No. 18818760.3 dated Mar. 31, 2021.
International Search Report and Written Opinion in International Application No. PCT/US2018/037614, dated Sep. 12, 2018.
Luangthonkam et al. "Addition of Cellulolytic Enzymes and Phytase for Improving Ethanol Fermentation Performance and Oil Recovery in Corn Dry Grind Process," Industrial Crops and Products, Dec. 23, 2015, vol. 77, pp. 803-808.
Richardson et al. "A Novel, High Performance Enzyme for Starch Liquefaction," Journal of Biological Chemistry, Jul. 19, 2002, vol. 277, No. 29, pp. 26501-26507.
Needleman and Wunsch, "A General Method Applicable to the Search for Similarities in the Amino Acid Sequence of Two Proteins," 1970, J. Mol. Biol. 48: 443-453.

* cited by examiner

*Primary Examiner* — Tekchand Saidha
(74) *Attorney, Agent, or Firm* — Sterne, Kessler, Goldstein & Fox P.L.L.C.

(57) ABSTRACT

A method for increasing the oil yield in an ethanol production process comprising: adding a liquid enzyme formulation having at least one enzyme, a buffering agent, a stabilizer, and a preservative wherein the pH of the enzyme formulation is about pH 6.0-8.0 to a beer, a distillation, a whole stillage, a centrifugation, a thin stillage, an evaporator, a syrup, or an oil recovery unit.

15 Claims, 8 Drawing Sheets
Specification includes a Sequence Listing.

SEQUENCE LISTING

<160> NUMBER OF SEQ ID NOS: 14

<210> SEQ ID NO 1
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetically generated

<400> SEQUENCE: 1

Met Ala Lys Tyr Ser Glu Leu Glu Lys Gly Gly Val Ile Met Gln Ala
1               5                   10                  15

Phe Tyr Trp Asp Val Pro Ser Gly Gly Ile Trp Trp Asp Thr Ile Arg
                20                  25                  30

Gln Lys Ile Pro Glu Trp Tyr Asp Ala Gly Ile Ser Ala Ile Trp Ile
            35                  40                  45

Pro Pro Ala Ser Lys Gly Met Gly Gly Ala Tyr Ser Met Gly Tyr Asp
        50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Glu Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 2
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetically generated peptide

<400> SEQUENCE: 2

```
Met Ala Lys Tyr Leu Glu Leu Glu Glu Gly Val Ile Met Gln Ala
 1               5                  10                  15

Phe Tyr Trp Asp Val Pro Ser Gly Gly Ile Trp Trp Asp Thr Ile Arg
             20                  25                  30

Gln Lys Ile Pro Glu Trp Tyr Asp Ala Gly Ile Ser Ala Ile Trp Ile
         35                  40                  45

Pro Pro Ala Ser Lys Gly Met Gly Gly Ala Tyr Ser Met Gly Tyr Asp
     50                  55                  60

Pro Tyr Asp Phe Phe Asp Leu Gly Glu Tyr Asp Gln Lys Gly Thr Val
 65                  70                  75                  80

Glu Thr Arg Phe Gly Ser Lys Gln Glu Leu Val Asn Met Ile Asn Thr
                 85                  90                  95

Ala His Ala Tyr Gly Ile Lys Val Ile Ala Asp Ile Val Ile Asn His
             100                 105                 110

Arg Ala Gly Gly Asp Leu Glu Trp Asn Pro Phe Val Gly Asp Tyr Thr
             115                 120                 125

Trp Thr Asp Phe Ser Lys Val Ala Ser Gly Lys Tyr Thr Ala Asn Tyr
         130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                 165                 170                 175

Leu Trp Ala Ser Gln Glu Ser Tyr Ala Ala Tyr Leu Arg Ser Ile Gly
             180                 185                 190

Ile Asp Ala Trp Arg Phe Asp Tyr Val Lys Gly Tyr Ala Pro Trp Val
             195                 200                 205

Val Lys Asp Trp Leu Asn Trp Trp Gly Gly Trp Ala Val Gly Glu Tyr
         210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                 245                 250                 255

Asp Asn Lys Asn Ile Pro Ala Leu Val Ser Ala Leu Gln Asn Gly Gln
             260                 265                 270

Thr Val Val Ser Arg Asp Pro Phe Lys Ala Val Thr Phe Val Ala Asn
         275                 280                 285

His Asp Thr Asp Ile Ile Trp Asn Lys Tyr Pro Ala Tyr Ala Phe Ile
     290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                 325                 330                 335

Leu Ala Gly Gly Ser Thr Asp Ile Val Tyr Tyr Asp Asn Asp Glu Leu
             340                 345                 350

Ile Phe Val Arg Asn Gly Tyr Gly Ser Lys Pro Gly Leu Ile Thr Tyr
             355                 360                 365

Ile Asn Leu Ala Ser Ser Lys Ala Gly Arg Trp Val Tyr Val Pro Lys
         370                 375                 380

Phe Ala Gly Ala Cys Ile His Glu Tyr Thr Gly Asn Leu Gly Gly Trp
385                 390                 395                 400
```

```
Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 3
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetically generated peptide

<400> SEQUENCE: 3

Met Ala Lys Tyr Ser Glu Leu Glu Glu Gly Val Ile Met Gln Ala
1               5                   10                  15

Phe Tyr Trp Asp Val Pro Gly Gly Ile Trp Trp Asp Thr Ile Arg
                20                  25                  30

Ser Lys Ile Pro Glu Trp Tyr Glu Ala Gly Ile Ser Ala Ile Trp Ile
            35                  40                  45

Pro Pro Ala Ser Lys Gly Met Gly Gly Ala Tyr Ser Met Gly Tyr Asp
        50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
                100                 105                 110

Arg Ala Gly Gly Asp Leu Glu Trp Asn Pro Phe Val Asn Asp Tyr Thr
            115                 120                 125

Trp Thr Asp Phe Ser Lys Val Ala Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Leu Ala Tyr Ala Phe Ile
290                 295                 300
```

Leu Thr Tyr Glu Gly Gln Pro Val Ile Phe Tyr Arg Asp His Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
            355                 360                 365

Ile Asn Leu Gly Ser Ser Lys Ala Gly Arg Trp Val Tyr Val Pro Lys
        370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 4
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetically generated peptide

<400> SEQUENCE: 4

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Arg Val
        195                 200                 205

Val Lys Asp Trp Leu Asn Trp Trp Gly Gly Trp Ala Val Gly Glu Tyr
            210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
            245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
            290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
            325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
            405                 410                 415

Ala His Asp Pro Ala Asn Gly Gln Tyr Gly Tyr Ser Val Trp Ser Tyr
            420                 425                 430

Cys Gly Val Gly
            435

<210> SEQ ID NO 5
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetically generated peptide

<400> SEQUENCE: 5

Met Ala Lys Tyr Leu Glu Leu Glu Glu Gly Gly Leu Ile Met Gln Ala
1               5                   10                  15

Phe Tyr Trp Asp Val Pro Met Gly Gly Ile Trp Trp Asp Thr Val Ala
            20                  25                  30

Gln Lys Ile Pro Asp Trp Ala Ser Ala Gly Ile Ser Ala Ile Trp Ile
            35                  40                  45

Pro Pro Ala Ser Lys Gly Met Gly Gly Ala Tyr Ser Met Gly Tyr Asp
50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
            85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
            115                 120                 125

Trp Thr Asp Phe Ser Lys Val Val Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Leu Ala Tyr Ala Phe Ile
    290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 6
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetically generated peptide

<400> SEQUENCE: 6

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Asp Thr Ile Arg
            20                  25                  30

Gln Lys Ile Pro Glu Trp Tyr Asp Ala Gly Ile Ser Ala Ile Trp Ile
            35                  40                  45

Pro Pro Ala Ser Lys Gly Met Gly Gly Ala Tyr Ser Met Gly Tyr Asp
50                      55                  60

Pro Tyr Asp Phe Phe Asp Leu Gly Glu Tyr Asp Gln Lys Gly Thr Val
65                      70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
                100                 105                 110

Arg Ala Gly Gly Asp Leu Glu Trp Asn Pro Phe Val Gly Asp Tyr Thr
            115                 120                 125

Trp Thr Asp Phe Ser Lys Val Ala Ser Gly Lys Tyr Thr Ala Asn Tyr
    130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
                180                 185                 190

Val Asp Ala Trp Arg Phe Asp Tyr Val Lys Gly Tyr Gly Ala Trp Val
            195                 200                 205

Val Lys Asp Trp Leu Asp Trp Trp Gly Trp Ala Val Gly Glu Tyr
            210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
                355                 360                 365

Ile Asn Leu Gly Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
            405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 7
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetically generated peptide

<400> SEQUENCE: 7

Met Ala Lys Tyr Ser Glu Leu Glu Glu Gly Val Ile Met Gln Ala
1               5                   10                  15

Phe Tyr Trp Asp Val Pro Ser Gly Gly Ile Trp Trp Asp Thr Ile Arg
                20                  25                  30

Gln Lys Ile Pro Glu Trp Tyr Asp Ala Gly Ile Ser Ala Ile Trp Ile
            35                  40                  45

Pro Pro Ala Ser Lys Gly Met Ser Gly Gly Tyr Ser Met Gly Tyr Asp
        50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
        275                 280                 285

His Asp Thr Asp Ile Ile Trp Thr Lys Tyr Leu Ala Tyr Ala Phe Ile
290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

```
Leu Ala Gly Gly Ser Thr Asp Ile Val Tyr Tyr Asp Asn Asp Glu Leu
                340                 345                 350

Ile Phe Val Arg Asn Gly Tyr Gly Asp Lys Pro Gly Leu Ile Thr Tyr
            355                 360                 365

Ile Asn Leu Gly Ser Ser Lys Ala Gly Arg Trp Val Tyr Val Pro Lys
        370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
            435

<210> SEQ ID NO 8
<211> LENGTH: 461
<212> TYPE: PRT
<213> ORGANISM: Unknown
<220> FEATURE:
<223> OTHER INFORMATION: Description of Unknown: Obtained from
      envrionmental sample

<400> SEQUENCE: 8

Met Lys Pro Ala Lys Leu Leu Val Phe Val Leu Val Ser Ile Leu
1               5                   10                  15

Ala Gly Leu Tyr Ala Gln Pro Ala Gly Ala Lys Tyr Leu Glu Leu
            20                  25                  30

Glu Glu Gly Gly Val Ile Met Gln Ala Phe Tyr Trp Asp Val Pro Ser
        35                  40                  45

Gly Gly Ile Trp Trp Asp Thr Ile Arg Gln Lys Ile Pro Glu Trp Tyr
    50                  55                  60

Asp Ala Gly Ile Ser Ala Ile Trp Ile Pro Pro Ala Ser Lys Gly Met
65                  70                  75                  80

Gly Gly Ala Tyr Ser Met Gly Tyr Asp Pro Tyr Asp Phe Phe Asp Leu
                85                  90                  95

Gly Glu Tyr Asp Gln Lys Gly Thr Val Glu Thr Arg Phe Gly Ser Lys
            100                 105                 110

Gln Glu Leu Val Asn Met Ile Asn Thr Ala His Ala Tyr Gly Ile Lys
        115                 120                 125

Val Ile Ala Asp Ile Val Ile Asn His Arg Ala Gly Gly Asp Leu Glu
130                 135                 140

Trp Asn Pro Phe Val Asn Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
                165                 170                 175

Val Lys Cys Cys Asp Glu Gly Thr Phe Gly Gly Phe Pro Asp Ile Ala
            180                 185                 190

His Glu Lys Ser Trp Asp Gln Tyr Trp Leu Trp Ala Ser Asn Glu Ser
        195                 200                 205

Tyr Ala Ala Tyr Leu Arg Ser Ile Gly Val Asp Ala Trp Arg Phe Asp
210                 215                 220

Tyr Val Lys Gly Tyr Gly Ala Trp Val Val Lys Asp Trp Leu Asp Trp
225                 230                 235                 240

Trp Gly Gly Trp Ala Val Gly Glu Tyr Trp Asp Thr Asn Val Asp Ala
                245                 250                 255
```

```
Leu Leu Asn Trp Ala Tyr Ser Ser Asp Ala Lys Val Phe Asp Phe Pro
            260                 265                 270

Leu Tyr Tyr Lys Met Asp Ala Ala Phe Asp Asn Lys Asn Ile Pro Ala
        275                 280                 285

Leu Val Glu Ala Leu Lys Asn Gly Gly Thr Val Val Ser Arg Asp Pro
    290                 295                 300

Phe Lys Ala Val Thr Phe Val Ala Asn His Asp Thr Asp Ile Ile Trp
305                 310                 315                 320

Asn Lys Tyr Pro Ala Tyr Ala Phe Ile Leu Thr Tyr Glu Gly Gln Pro
                325                 330                 335

Thr Ile Phe Tyr Arg Asp Tyr Glu Glu Trp Leu Asn Lys Asp Arg Leu
            340                 345                 350

Lys Asn Leu Ile Trp Ile His Asp His Leu Ala Gly Gly Ser Thr Asp
        355                 360                 365

Ile Val Tyr Tyr Asp Asn Asp Glu Leu Ile Phe Val Arg Asn Gly Tyr
    370                 375                 380

Gly Asp Lys Pro Gly Leu Ile Thr Tyr Ile Asn Leu Gly Ser Ser Lys
385                 390                 395                 400

Ala Gly Arg Trp Val Tyr Val Pro Lys Phe Ala Gly Ala Cys Ile His
                405                 410                 415

Glu Tyr Thr Gly Asn Leu Gly Gly Trp Val Asp Lys Trp Val Asp Ser
            420                 425                 430

Ser Gly Trp Val Tyr Leu Glu Ala Pro Ala His Asp Pro Ala Asn Gly
        435                 440                 445

Tyr Tyr Gly Tyr Ser Val Trp Ser Tyr Cys Gly Val Gly
    450                 455                 460

<210> SEQ ID NO 9
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetically generated peptide

<400> SEQUENCE: 9

Met Ala Lys Tyr Thr Glu Leu Glu Glu Gly Gly Val Ile Met Gln Ala
1               5                   10                  15

Phe Tyr Trp Asp Val Pro Gly Gly Gly Ile Trp Trp Asp Thr Ile Arg
            20                  25                  30

Ser Lys Ile Pro Glu Trp Tyr Glu Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
            85                  90                  95

Ala His Ala Tyr Gly Met Lys Val Ile Ala Asp Ile Val Ile Asn His
        100                 105                 110

Arg Ala Gly Gly Asp Leu Glu Trp Asn Pro Phe Val Asn Asp Tyr Thr
    115                 120                 125

Trp Thr Asp Phe Ser Lys Val Ala Ser Gly Lys Tyr Thr Ala Asn Tyr
130                 135                 140
```

-continued

```
Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
            165                 170                 175

Leu Trp Ala Ser Asp Glu Ser Tyr Ala Ala Tyr Leu Arg Ser Ile Gly
        180                 185                 190

Val Asp Ala Trp Arg Phe Asp Tyr Val Lys Gly Tyr Gly Ala Trp Val
    195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Leu Ala Tyr Ala Phe Ile
    290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
370                 375                 380

Phe Ala Gly Pro Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 10
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetically generated peptide

<400> SEQUENCE: 10

Met Ala Lys Tyr Ser Glu Leu Glu Gly Gly Leu Ile Met Gln Ala
1               5                   10                  15

Phe Tyr Trp Asp Val Pro Met Gly Gly Ile Trp Trp Asp Thr Ile Ala
                20                  25                  30

Gln Lys Ile Pro Asp Trp Ala Ser Ala Gly Ile Ser Ala Ile Trp Ile
            35                  40                  45
```

Pro Pro Ala Ser Lys Gly Met Gly Gly Ala Tyr Ser Met Gly Tyr Asp
50                  55                  60

Pro Tyr Asp Phe Phe Asp Leu Gly Glu Tyr Asp Gln Glu Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
        195                 200                 205

Val Lys Asp Trp Leu Asp Trp Trp Gly Gly Trp Ala Val Gly Glu Tyr
    210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
    370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 11
<211> LENGTH: 432

```
<212> TYPE: PRT
<213> ORGANISM: Unknown
<220> FEATURE:
<223> OTHER INFORMATION: Description of Unknown: Obtained from an
      environmental sample

<400> SEQUENCE: 11
```

| | | | | | | | | | | | | | | |
|---|---|---|---|---|---|---|---|---|---|---|---|---|---|---|
| Met | Ala | Leu | Glu | Glu | Gly | Gly | Leu | Ile | Met | Gln | Ala | Phe | Tyr | Trp | Asp |
| 1 | | | | 5 | | | | | 10 | | | | | 15 |
| Val | Pro | Gly | Gly | Gly | Ile | Trp | Trp | Asp | Thr | Ile | Ala | Gln | Lys | Ile | Pro |
| | | | 20 | | | | | 25 | | | | | 30 | |
| Asp | Trp | Ala | Ser | Ala | Gly | Ile | Ser | Ala | Ile | Trp | Ile | Pro | Pro | Ala | Ser |
| | | 35 | | | | | 40 | | | | | 45 | | | |
| Lys | Gly | Met | Ser | Gly | Gly | Tyr | Ser | Met | Gly | Tyr | Asp | Pro | Tyr | Asp | Phe |
| 50 | | | | | 55 | | | | | 60 | | | | | |
| Phe | Asp | Leu | Gly | Glu | Tyr | Tyr | Gln | Lys | Gly | Ser | Val | Glu | Thr | Arg | Phe |
| 65 | | | | | 70 | | | | | 75 | | | | | 80 |
| Gly | Ser | Lys | Glu | Glu | Leu | Val | Asn | Met | Ile | Asn | Thr | Ala | His | Ala | His |
| | | | | 85 | | | | | 90 | | | | | 95 | |
| Asn | Met | Lys | Val | Ile | Ala | Asp | Ile | Val | Ile | Asn | His | Arg | Ala | Gly | Gly |
| | | | 100 | | | | | 105 | | | | | 110 | | |
| Asp | Leu | Glu | Trp | Asn | Pro | Phe | Thr | Asn | Ser | Tyr | Thr | Trp | Thr | Asp | Phe |
| | | 115 | | | | | 120 | | | | | 125 | | | |
| Ser | Lys | Val | Ala | Ser | Gly | Lys | Tyr | Thr | Ala | Asn | Tyr | Leu | Asp | Phe | His |
| 130 | | | | | 135 | | | | | 140 | | | | | |
| Pro | Asn | Glu | Leu | His | Ala | Gly | Asp | Ser | Gly | Thr | Phe | Gly | Gly | Tyr | Pro |
| 145 | | | | | 150 | | | | | 155 | | | | | 160 |
| Asp | Ile | Cys | His | Asp | Lys | Ser | Trp | Asp | Gln | His | Trp | Leu | Trp | Ala | Ser |
| | | | 165 | | | | | 170 | | | | | 175 | | |
| Asn | Glu | Ser | Tyr | Ala | Ala | Tyr | Leu | Arg | Ser | Ile | Gly | Ile | Asp | Ala | Trp |
| | | | | 180 | | | | | 185 | | | | | 190 | |
| Arg | Phe | Asp | Tyr | Val | Lys | Gly | Tyr | Ala | Pro | Trp | Val | Val | Lys | Asn | Trp |
| | | | 195 | | | | | 200 | | | | | 205 | | |
| Leu | Asn | Arg | Trp | Gly | Gly | Trp | Ala | Val | Gly | Glu | Tyr | Trp | Asp | Thr | Asn |
| 210 | | | | | 215 | | | | | 220 | | | | | |
| Val | Asp | Ala | Leu | Leu | Ser | Trp | Ala | Tyr | Asp | Ser | Gly | Ala | Lys | Val | Phe |
| 225 | | | | | 230 | | | | | 235 | | | | | 240 |
| Asp | Phe | Pro | Leu | Tyr | Tyr | Lys | Met | Asp | Glu | Ala | Phe | Asp | Asn | Asn | Asn |
| | | | | 245 | | | | | 250 | | | | | 255 | |
| Ile | Pro | Ala | Leu | Val | Asp | Ala | Leu | Lys | Asn | Gly | Gly | Thr | Val | Val | Ser |
| | | | 260 | | | | | 265 | | | | | 270 | | |
| Arg | Asp | Pro | Phe | Lys | Ala | Val | Thr | Phe | Val | Ala | Asn | His | Asp | Thr | Asn |
| | | 275 | | | | | 280 | | | | | 285 | | | |
| Ile | Ile | Trp | Asn | Lys | Tyr | Pro | Ala | Tyr | Ala | Phe | Ile | Leu | Thr | Tyr | Glu |
| | 290 | | | | | 295 | | | | | 300 | | | | |
| Gly | Gln | Pro | Ala | Ile | Phe | Tyr | Arg | Asp | Tyr | Glu | Glu | Trp | Leu | Asn | Lys |
| 305 | | | | | 310 | | | | | 315 | | | | | 320 |
| Asp | Arg | Leu | Arg | Asn | Leu | Ile | Trp | Ile | His | Asp | His | Leu | Ala | Gly | Gly |
| | | | | 325 | | | | | 330 | | | | | 335 | |
| Ser | Thr | Asp | Ile | Ile | Tyr | Tyr | Asp | Ser | Asp | Glu | Leu | Ile | Phe | Val | Arg |
| | | | 340 | | | | | 345 | | | | | 350 | | |
| Asn | Gly | Tyr | Gly | Asp | Lys | Pro | Gly | Leu | Ile | Thr | Tyr | Ile | Asn | Leu | Gly |
| | | 355 | | | | | 360 | | | | | 365 | | | |
| Ser | Ser | Lys | Ala | Gly | Arg | Trp | Val | Tyr | Val | Pro | Lys | Phe | Ala | Gly | Ser |
| 370 | | | | | 375 | | | | | 380 | | | | | |

```
Cys Ile His Glu Tyr Thr Gly Asn Leu Gly Gly Trp Ile Asp Lys Trp
385                 390                 395                 400

Val Asp Ser Ser Gly Arg Val Tyr Leu Glu Ala Pro Ala His Asp Pro
                405                 410                 415

Ala Asn Gly Gln Tyr Gly Tyr Ser Val Trp Ser Tyr Cys Gly Val Gly
                420                 425                 430

<210> SEQ ID NO 12
<211> LENGTH: 471
<212> TYPE: PRT
<213> ORGANISM: Unknown
<220> FEATURE:
<223> OTHER INFORMATION: Description of Unknown: Obtained from an
      environmental sample

<400> SEQUENCE: 12

Met Pro Ala Phe Lys Ser Lys Val Met His Met Lys Leu Lys Tyr Leu
1               5                   10                  15

Ala Leu Val Leu Leu Ala Val Ala Ser Ile Gly Leu Leu Ser Thr Pro
                20                  25                  30

Val Gly Ala Ala Lys Tyr Ser Glu Leu Glu Glu Gly Gly Val Ile Met
            35                  40                  45

Gln Ala Phe Tyr Trp Asp Val Pro Thr Gly Gly Ile Trp Trp Asp Thr
    50                  55                  60

Ile Arg Gln Lys Ile Pro Glu Trp Tyr Asp Ala Gly Ile Ser Ala Ile
65                  70                  75                  80

Trp Ile Pro Pro Ala Ser Lys Gly Met Gly Gly Ala Tyr Ser Met Gly
                85                  90                  95

Tyr Asp Pro Tyr Asp Phe Phe Asp Leu Gly Glu Tyr Tyr Gln Lys Gly
                100                 105                 110

Thr Val Glu Thr Arg Phe Gly Ser Lys Glu Glu Leu Val Asn Met Ile
            115                 120                 125

Asn Thr Ala His Ser Tyr Gly Ile Lys Val Ile Ala Asp Ile Val Ile
130                 135                 140

Asn His Arg Ala Gly Gly Asp Leu Glu Trp Asn Pro Phe Val Asn Asn
145                 150                 155                 160

Tyr Thr Trp Thr Asp Phe Ser Lys Val Ala Ser Gly Lys Tyr Thr Ala
                165                 170                 175

Asn Tyr Leu Asp Phe His Pro Asn Glu Val Lys Cys Cys Asp Glu Gly
                180                 185                 190

Thr Phe Gly Asp Phe Pro Asp Ile Ala His Glu Lys Ser Trp Asp Gln
            195                 200                 205

Tyr Trp Leu Trp Ala Ser Asn Glu Ser Tyr Ala Ala Tyr Leu Arg Ser
    210                 215                 220

Ile Gly Ile Asp Ala Trp Arg Phe Asp Tyr Val Lys Gly Tyr Gly Ala
225                 230                 235                 240

Trp Val Val Asn Asp Trp Leu Ser Trp Trp Gly Gly Trp Ala Val Gly
                245                 250                 255

Glu Tyr Trp Asp Thr Asn Val Asp Ala Leu Leu Asn Trp Ala Tyr Asn
                260                 265                 270

Ser Gly Ala Lys Val Phe Asp Phe Pro Leu Tyr Tyr Lys Met Asp Glu
            275                 280                 285

Ala Phe Asp Asn Thr Asn Ile Pro Ala Leu Val Tyr Ala Leu Gln Asn
    290                 295                 300
```

```
Gly Gly Thr Val Val Ser Arg Asp Pro Phe Lys Ala Val Thr Phe Val
305                 310                 315                 320

Ala Asn His Asp Thr Asp Ile Ile Trp Asn Lys Tyr Pro Ala Tyr Ala
                325                 330                 335

Phe Ile Leu Thr Tyr Glu Gly Gln Pro Val Ile Phe Tyr Arg Asp Tyr
            340                 345                 350

Glu Glu Trp Leu Asn Lys Asp Lys Leu Asn Asn Leu Ile Trp Ile His
        355                 360                 365

Glu His Leu Ala Gly Gly Ser Thr Lys Ile Leu Tyr Tyr Asp Asn Asp
    370                 375                 380

Glu Leu Ile Phe Met Arg Glu Gly Tyr Gly Ser Lys Pro Gly Leu Ile
385                 390                 395                 400

Thr Tyr Ile Asn Leu Gly Asn Asp Trp Ala Glu Arg Trp Val Asn Val
                405                 410                 415

Gly Ser Lys Phe Ala Gly Tyr Thr Ile His Glu Tyr Thr Gly Asn Leu
            420                 425                 430

Gly Gly Trp Val Asp Arg Trp Val Gln Tyr Asp Gly Trp Val Lys Leu
        435                 440                 445

Thr Ala Pro Pro His Asp Pro Ala Asn Gly Tyr Tyr Gly Tyr Ser Val
    450                 455                 460

Trp Ser Tyr Ala Gly Val Gly
465                 470

<210> SEQ ID NO 13
<211> LENGTH: 464
<212> TYPE: PRT
<213> ORGANISM: Unknown
<220> FEATURE:
<223> OTHER INFORMATION: Description of Unknown: Obtained from an
      environmental sample

<400> SEQUENCE: 13

Val Val His Met Lys Leu Lys Tyr Leu Ala Leu Val Leu Leu Ala Val
1               5                   10                  15

Ala Ser Ile Gly Leu Leu Ser Thr Pro Val Gly Ala Ala Lys Tyr Ser
            20                  25                  30

Glu Leu Glu Glu Gly Gly Val Ile Met Gln Ala Phe Tyr Trp Asp Val
        35                  40                  45

Pro Gly Gly Gly Ile Trp Trp Asp Thr Ile Arg Gln Lys Ile Pro Glu
    50                  55                  60

Trp Tyr Asp Ala Gly Ile Ser Ala Ile Trp Ile Pro Pro Ala Ser Lys
65                  70                  75                  80

Gly Met Gly Gly Gly Tyr Ser Met Gly Tyr Asp Pro Tyr Asp Phe Phe
                85                  90                  95

Asp Leu Gly Glu Tyr Tyr Gln Lys Gly Thr Val Glu Thr Arg Phe Gly
            100                 105                 110

Ser Lys Glu Glu Leu Val Asn Met Ile Asn Thr Ala His Ser Tyr Gly
        115                 120                 125

Ile Lys Val Ile Ala Asp Ile Val Ile Asn His Arg Ala Gly Gly Asp
    130                 135                 140

Leu Glu Trp Asn Pro Phe Val Asn Asn Tyr Thr Trp Thr Asp Phe Ser
145                 150                 155                 160

Lys Val Ala Ser Gly Lys Tyr Thr Ala Asn Tyr Leu Asp Phe His Pro
                165                 170                 175
```

```
Asn Glu Val Lys Cys Cys Asp Glu Gly Thr Phe Gly Asp Phe Pro Asp
        180                 185                 190

Ile Ala His Glu Lys Ser Trp Asp Gln Tyr Trp Leu Trp Ala Ser Asn
        195                 200                 205

Glu Ser Tyr Ala Ala Tyr Leu Arg Ser Ile Gly Ile Asp Ala Trp Arg
210                 215                 220

Phe Asp Tyr Val Lys Gly Tyr Gly Ala Trp Val Val Asn Asp Trp Leu
225                 230                 235                 240

Ser Trp Trp Gly Gly Trp Ala Val Gly Glu Tyr Trp Asp Thr Asn Val
                245                 250                 255

Asp Ala Leu Leu Asn Trp Ala Tyr Asp Ser Gly Ala Lys Val Phe Asp
        260                 265                 270

Phe Pro Leu Tyr Tyr Lys Met Asp Glu Ala Phe Asp Asn Thr Asn Ile
        275                 280                 285

Pro Ala Leu Val Tyr Ala Leu Gln Asn Gly Gly Thr Val Val Ser Arg
        290                 295                 300

Asp Pro Phe Lys Ala Val Thr Phe Val Ala Asn His Asp Thr Asp Ile
305                 310                 315                 320

Ile Trp Asn Lys Tyr Pro Ala Tyr Ala Phe Ile Leu Thr Tyr Glu Gly
                325                 330                 335

Gln Pro Val Ile Phe Tyr Arg Asp Tyr Glu Glu Trp Leu Asn Lys Asp
                340                 345                 350

Lys Leu Asn Asn Leu Ile Trp Ile His Glu His Leu Ala Gly Gly Ser
                355                 360                 365

Thr Lys Ile Leu Tyr Tyr Asp Asn Asp Glu Leu Ile Phe Met Arg Glu
        370                 375                 380

Gly Tyr Gly Ser Lys Pro Gly Leu Ile Thr Tyr Ile Asn Leu Gly Asn
385                 390                 395                 400

Asp Trp Ala Glu Arg Trp Val Asn Val Gly Ser Lys Phe Ala Gly Tyr
                405                 410                 415

Thr Ile His Glu Tyr Thr Gly Asn Leu Gly Gly Trp Val Asp Arg Trp
                420                 425                 430

Val Gln Tyr Asp Gly Trp Val Lys Leu Thr Ala Pro Pro His Asp Pro
        435                 440                 445

Ala Asn Gly Tyr Tyr Gly Tyr Ser Val Trp Ser Tyr Ala Gly Val Gly
        450                 455                 460

<210> SEQ ID NO 14
<211> LENGTH: 445
<212> TYPE: PRT
<213> ORGANISM: Unknown
<220> FEATURE:
<223> OTHER INFORMATION: Description of Unknown: Eukaryote sequence

<400> SEQUENCE: 14

Met Ala Lys Tyr Ser Glu Leu Glu Gln Gly Gly Val Ile Met Gln Ala
1               5                   10                  15

Phe Tyr Trp Asp Val Pro Glu Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Tyr Phe Asp Leu Gly Glu Phe Tyr Gln Lys Gly Thr Val
65                  70                  75                  80
```

```
Glu Thr Arg Phe Gly Ser Lys Glu Glu Leu Val Asn Met Ile Ser Thr
                85                  90                  95
Ala His Gln Tyr Gly Ile Lys Val Ile Ala Asp Ile Val Ile Asn His
            100                 105                 110
Arg Ala Gly Gly Asp Leu Glu Trp Asn Pro Tyr Val Gly Asp Tyr Thr
        115                 120                 125
Trp Thr Asp Phe Ser Lys Val Ala Ser Gly Lys Tyr Lys Ala His Tyr
    130                 135                 140
Met Asp Phe His Pro Asn Asn Tyr Ser Thr Ser Asp Glu Gly Thr Phe
145                 150                 155                 160
Gly Gly Phe Pro Asp Ile Asp His Leu Val Pro Phe Asn Gln Tyr Trp
            165                 170                 175
Leu Trp Ala Ser Asn Glu Ser Tyr Ala Ala Tyr Leu Arg Ser Ile Gly
                180                 185                 190
Ile Asp Ala Trp Arg Phe Asp Tyr Val Lys Gly Tyr Gly Ala Trp Val
            195                 200                 205
Val Lys Asp Trp Leu Ser Gln Trp Gly Gly Trp Ala Val Gly Glu Tyr
    210                 215                 220
Trp Asp Thr Asn Val Asp Ala Leu Leu Asn Trp Ala Tyr Ser Ser Gly
225                 230                 235                 240
Ala Lys Val Phe Asp Phe Pro Leu Tyr Tyr Lys Met Asp Glu Ala Phe
            245                 250                 255
Asp Asn Lys Asn Ile Pro Ala Leu Val Tyr Ala Ile Gln Asn Gly Glu
                260                 265                 270
Thr Val Val Ser Arg Asp Pro Phe Lys Ala Val Thr Phe Val Ala Asn
            275                 280                 285
His Asp Thr Asn Ile Ile Trp Asn Lys Tyr Pro Ala Tyr Ala Phe Ile
    290                 295                 300
Leu Thr Tyr Glu Gly Gln Pro Val Ile Phe Tyr Arg Asp Tyr Glu Glu
305                 310                 315                 320
Trp Leu Asn Lys Asp Lys Leu Asn Asn Leu Ile Trp Ile His Glu His
            325                 330                 335
Leu Ala Gly Gly Ser Thr Lys Ile Leu Tyr Tyr Asp Asp Asp Glu Leu
                340                 345                 350
Ile Phe Met Arg Glu Gly Tyr Gly Asp Arg Pro Gly Leu Ile Thr Tyr
            355                 360                 365
Ile Asn Leu Gly Ser Asp Trp Ala Glu Arg Trp Val Asn Val Gly Ser
    370                 375                 380
Lys Phe Ala Gly Tyr Thr Ile His Glu Tyr Thr Gly Asn Leu Gly Gly
385                 390                 395                 400
Trp Val Asp Arg Tyr Val Gln Tyr Asp Gly Trp Val Lys Leu Thr Ala
            405                 410                 415
Pro Pro His Asp Pro Ala Asn Gly Tyr Tyr Gly Tyr Ser Val Trp Ser
                420                 425                 430
Tyr Ala Gly Val Gly Arg Ser His His His His His His
            435                 440                 445
```

METHOD FOR INCREASING OIL YIELD DURING ETHANOL PRODUCTION

CROSS-REFERENCE TO RELATED APPLICATIONS

This application is a U.S. National Phase Application under 35 U.S.C. § 371 of International Application No. PCT/US2018/037614, filed on Jun. 14, 2018, which claims the benefit of U.S. Provisional Patent Application No. 62/520,998, filed on Jun. 16, 2017, each of which is incorporated herein by reference in its entirety.

REFERENCE TO SEQUENCE LISTING SUBMITTED VIA EFS-WEB

The instant application contains a Sequence Listing which has been submitted electronically in ASCII format and is hereby incorporated by reference in its entirety. Said ASCII copy, created on Apr. 5, 2021, is named 170872US02_BAF-20-1221US_SL.txt and is 55,519 bytes in size.

BACKGROUND

Ethanol production involves converting biomass to ethanol, which is then sold to the commercial market and can be used for blending with fuels that are can be used for automobiles, planes, boats, and other forms of transportation. In addition to producing ethanol, these commercial manufacturing plants also generate other products that are sold into commercial markets, for example carbon dioxide, dried distillers grains (DDG or DDGS), which is used for animal feed, and oil, which can be used for biofuels or cooking. Therefore, there is a need in ethanol production industry to increase yields of ethanol, carbon dioxide, dried distiller's grains, and oil.

One approach for increasing oil yields during ethanol production process to provide single enzymes that can increase the oil yield. Enzymes that can increase the yield include amylase, phytase, lipase, and any combination thereof. Enzyme performance in industrial applications are highly dependent upon the conditions under which they are expected to perform. These conditions include characteristics such as pH, temperature, enzyme activity, enzyme formulations, and different enzymes from a single class of enzymes can have different performance depending upon this conditions. The enzymes can be added at various parts of the ethanol production process. For example, FIG. 1, shows that the enzymes can be added to the slurry, liquification, fermentation, beer, distillation, whole stillage, centrifugation, thin stillage (backset), and/or oil recovery stage. Therefore, there is a need in art to identify enzymes and enzyme formulations that increase oil yields during ethanol production process.

The present disclosure relates to liquid enzyme formulations containing one or more alpha-amylases. Alpha-amylases are useful in a variety of industrial applications such as starch processing, production of a food product, a biofuel, a cleaning product, an animal feed, or a paper pulp, and enhanced oil recovery. The present disclosure further relates to methods of making and using a liquid enzyme formulation containing one or more enzymes, such as an alpha-amylase, a protease, a cellulase, a glucoamylase having improved stability.

Currently, some alpha-amylase formulations maintain the enzyme at a high pH (pH 10.7) environment. Alpha-amylases in high pH formulation may have a lowered stability at this high pH range, which can result in a shortened product shelf life. In addition, there are few stable, compatible, and regulatory approved buffering agents for a high pH formulation. Without a buffer, pH of the alpha-amylase formulation can be unstable, and may drift lower over time. Further, there is potential of microbial growth due to the lack of a functioning preservative because food grade preservatives do not work quite well in this pH range. While the high pH initially has some anti-microbial effect, the pH eventually drifts down. The formulation may also be incompatible with most of the common formulations of other enzyme products, which are usually in neutral or slightly acidic pH range. Sometimes it is advantageous to mix two alpha-amylases of different properties during starch hydrolysis. For example, mixing high temperature active alpha-amylase with a low temperature active alpha-amylase may increase the break down the starch into oligo saccharides and lower the viscosity of the feed stock. Due to the extreme pH difference of different enzyme formulations, it is difficult to blend an alpha-amylase with a high pH formulation with different enzyme(s) having a low pH formulation.

SUMMARY

A method for increasing the oil yield in an ethanol production process comprising: providing a liquid enzyme formulation having at least one enzyme, a buffering agent, a stabilizer, and a preservative wherein the pH of the enzyme formulation is from pH 6.0-8.0, and adding the liquid enzyme formulation to a beer, a distillation, a whole stillage, a centrifugation, a thin stillage, an evaporator, a syrup, or an oil recovery unit.

The liquid enzyme formulation of above, wherein the pH of the liquid enzyme formulation is about pH 6.3-6.7.

The liquid enzyme formulation of above, wherein the stabilizer comprises sucrose, sorbitol, mannitol, glycerol, trehalose, sodium chloride, sodium sulfate, or any combination thereof.

The liquid enzyme formulation of above, wherein the buffering agent comprises: sodium citrate, potassium citrate, citric acid, sodium acetate, acetic acid, sodium phosphate, potassium phosphate, or any combination thereof.

The liquid enzyme formulation of above, wherein the alpha-amylase retains at least 90% of its activity at a temperature of 4-40° C.

The liquid enzyme formulation of above, wherein the alpha-amylase retains at least 90% of its activity at a temperature of 25-30° C.

The liquid enzyme formulation of above, wherein the alpha-amylase retains at least 90% of its activity for 1 year.

The liquid enzyme formulation of above, wherein the alpha-amylase has a shelf life of at least 1 year.

The liquid enzyme formulation of above, wherein the alpha-amylase has a shelf life of at least 1 year at 25° C.

The liquid enzyme formulation of above, wherein the preservative comprises: potassium sorbate, sodium sorbate, sorbic acid, sodium benzoate, benzoic acid, methyl paraben, calcium propionate, sodium propionate, ammonium propionate, propionic acid, or any combination thereof.

The liquid enzyme formulation of above, further comprising at least two preservatives.

The liquid enzyme formulation of above, wherein the alpha-amylase comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to one of the amino acid sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

The liquid enzyme formulation of above, further comprising a second enzyme.

The liquid enzyme formulation of above, wherein the second enzyme is selected from the group consisting of a second alpha-amylase, a beta-amylase, a glucoamylase, a protease, a phytase, a pullulanase, a cellulase, a cellobiohydrolase, a beta-glucosidase, an endoglucanase, a mannanase, a xylanase, a lipase, a phospholipase, and any combination thereof.

The method of above, wherein a liquid enzyme formulation having at least one enzyme is added to a first stillage composition to form a second stillage composition, wherein the one or more alpha amylase enzymes are added to the first stillage composition in an amount from 0.001 to 0.01 grams/100 grams of solids of the first stillage composition; and obtaining oil from the second stillage composition.

The method described above, wherein the first stillage composition comprises whole stillage, thin stillage, wet cake and/or syrup.

DETAILED DESCRIPTION

Figure 1:
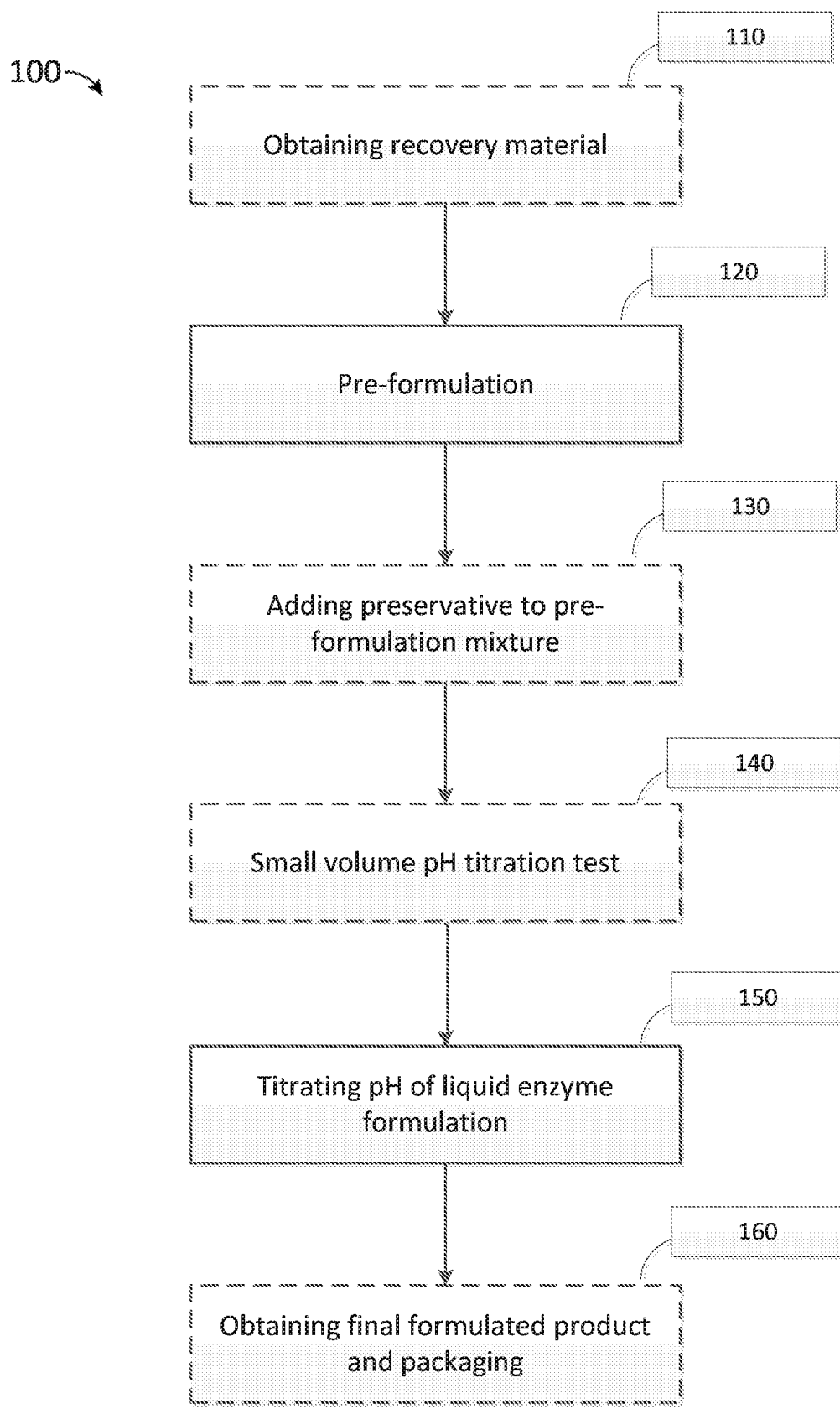
FIG. 1 shows an exemplary flowchart illustrating a non-limiting embodiment of the formulation process disclosed herein.
Figure 2:
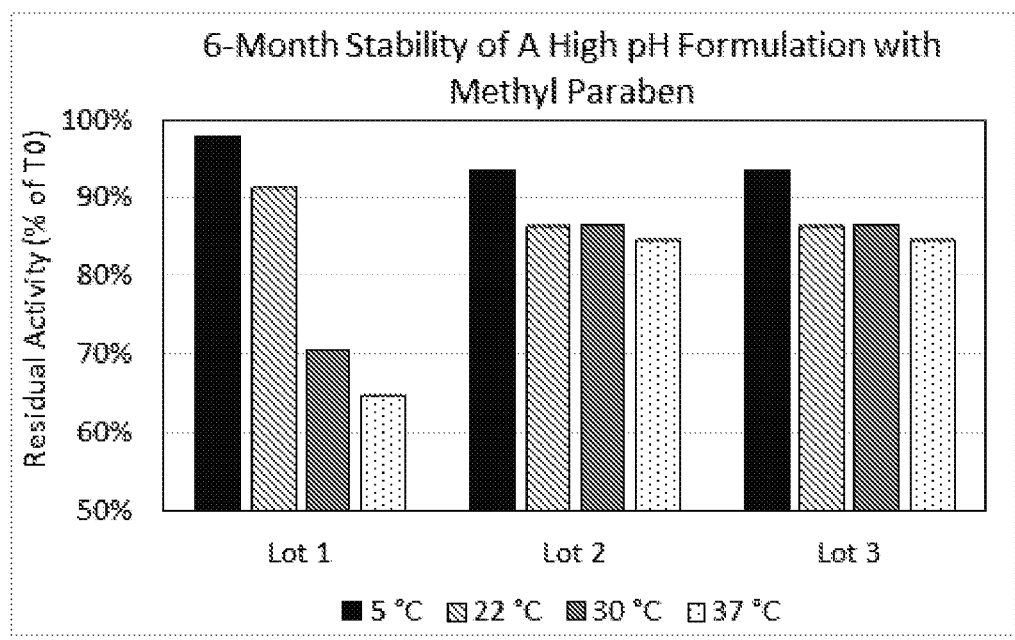
FIG. 2 shows enzyme stability of a high pH alpha-amylase enzyme formulation containing methyl paraben (three different production lots) at six months. The alpha-amylase enzyme formulation contains 40% glycerol, 0.1% methyl paraben, and pH 10.7. The samples were stored at 5° C., 22° C., 30° C. and 37° C., respectively.
Figure 3:
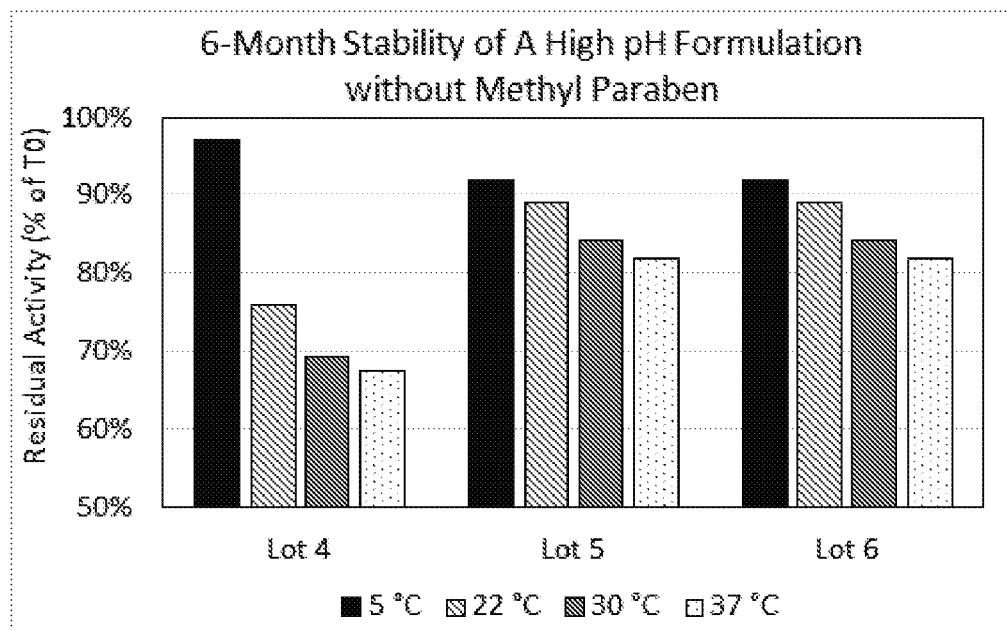
FIG. 3 shows enzyme stability of a high pH alpha-amylase enzyme formulation having no methyl paraben (three different production lots) at six months. The alpha-amylase enzyme formulation contains 40% glycerol, and pH 10.7. Various samples were stored at 5° C., 22° C., 30° C. and 37° C., respectively.
Figure 4A:
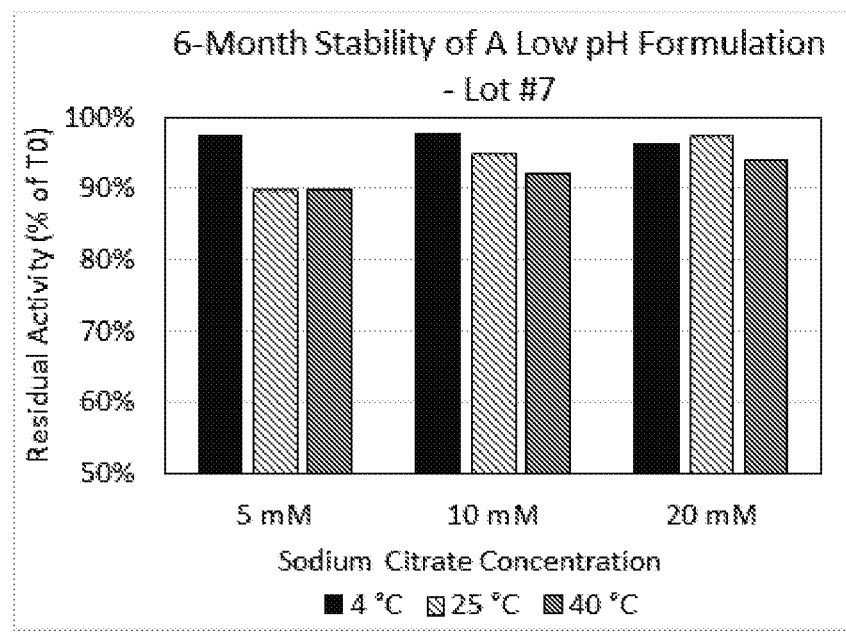
FIGS. 4A, 4B, & 4C show enzyme stability of an exemplary low pH alpha-amylase (SEQ ID NO:1) enzyme formulation (three different production lots) at six months. The alpha-amylase enzyme formulation contains 40% glycerol, 0.2% potassium sorbate, 0.1% methyl paraben, pH 6.5, and sodium citrate at 5 mM, 10 mM or 20 mM. The samples were stored at 4° C., 25° C. and 40° C., respectively.
Figure 4B:
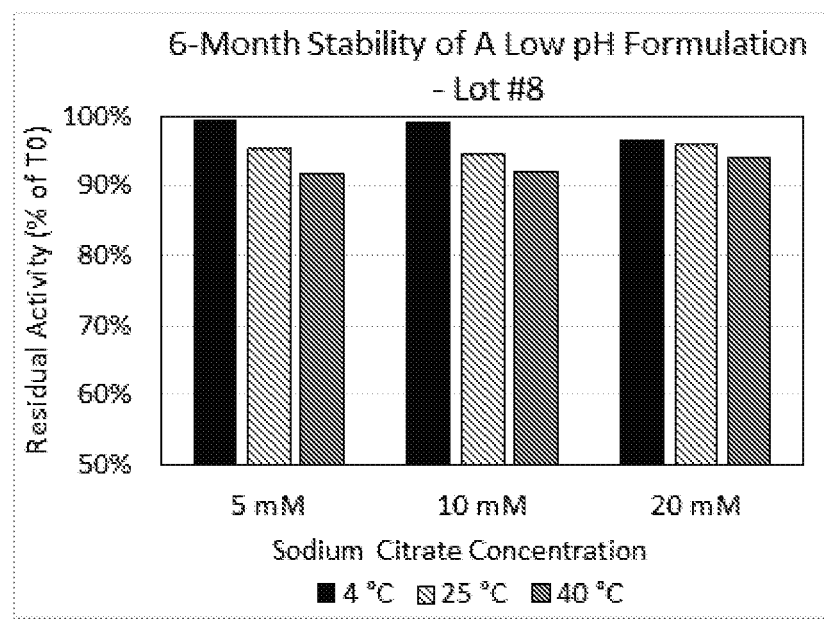
Figure 4C:
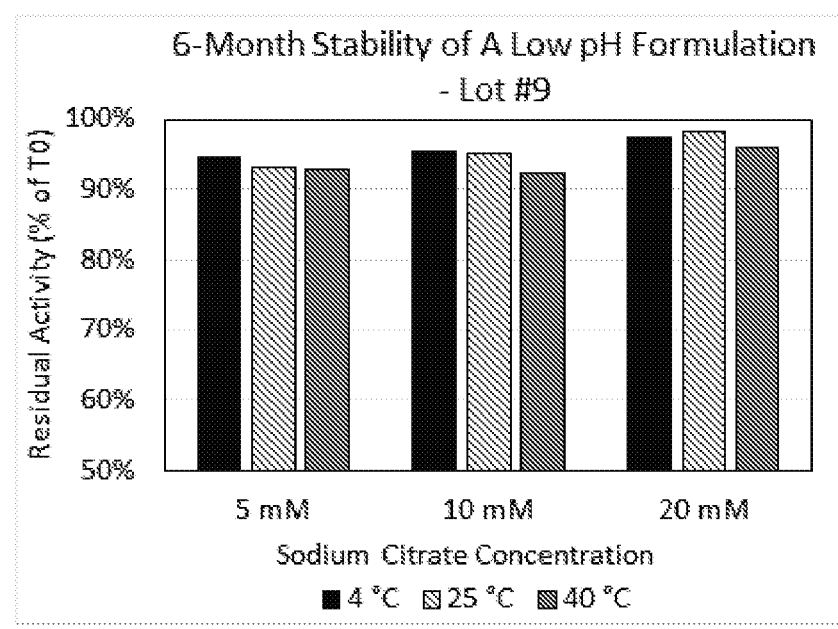
Figure 5A:
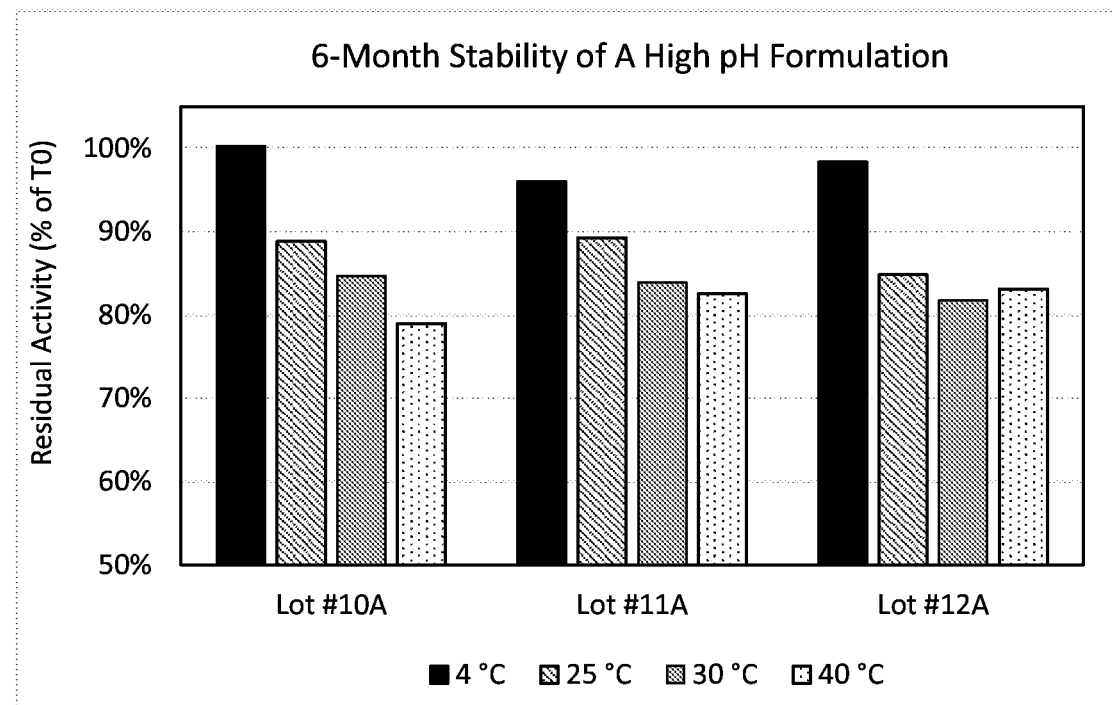
FIGS. 5A & 5B show the comparison of enzyme stability between alpha-amylase enzyme formulations at two different pH (three different production lots) at six months. The high pH alpha-amylase enzyme formulation contains 40% glycerol, 0.1% methyl paraben, and pH 10.7; the low pH alpha-amylase enzyme formulation contains 40% glycerol, 0.1% methyl paraben, 0.2% potassium sorbate, 10 mM sodium citrate, pH 6.5. Each of three enzyme production lots were formulated into the two different formulations. The samples were stored at 4° C., 25° C., 30° C. and 40° C., respectively.
Figure 5B:
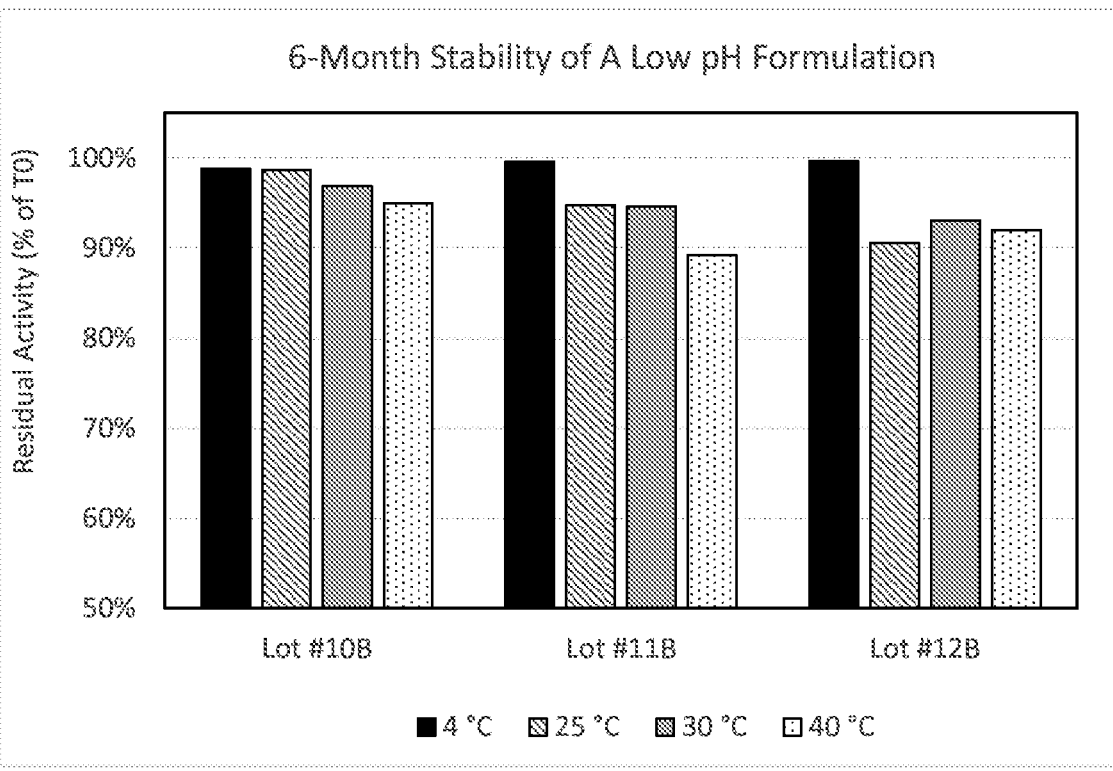
Figure 6:
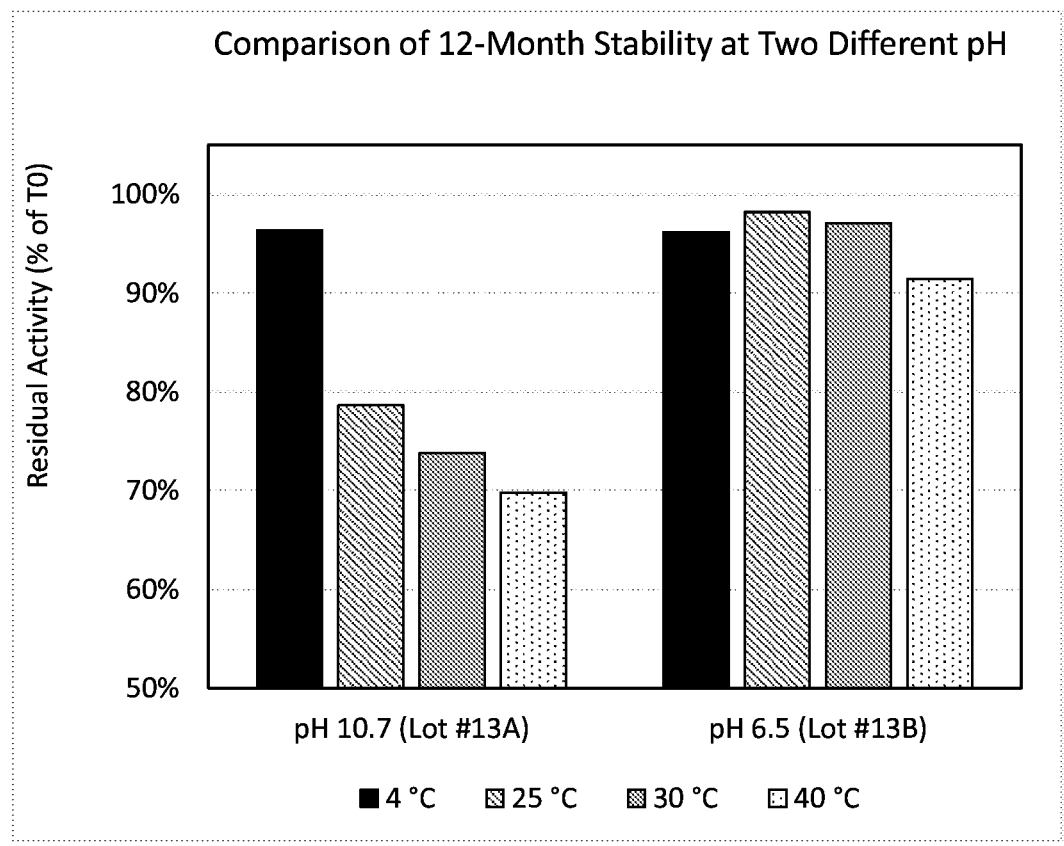
FIG. 6 shows the comparison of enzyme stability between alpha-amylase enzyme formulations at two different pH at twelve months. The high pH alpha-amylase enzyme formulation contains 40% glycerol, 0.1% methyl paraben, and pH 10.7; the low pH alpha-amylase enzyme formulation contains 40% glycerol, 0.1% methyl paraben, 0.2% potassium sorbate, 10 mM sodium citrate, pH 6.5. The same enzyme production lot was formulated into the two different formulations. The samples were stored at 4° C., 25° C., 30° C. and 40° C., respectively.
Figure 7A:
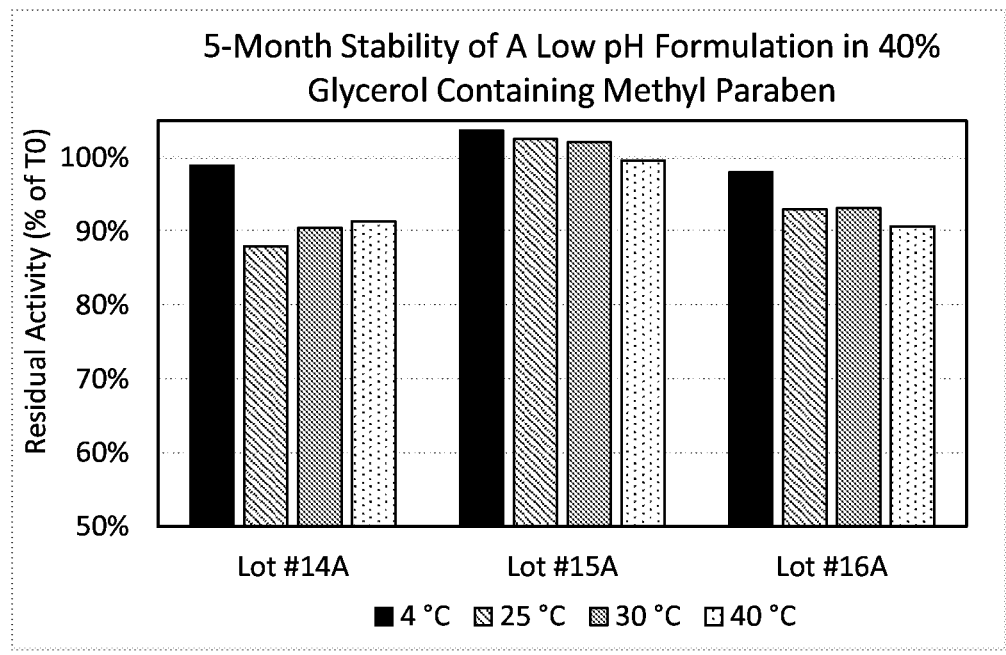
FIGS. 7A & 7B show the comparison of enzyme stability between two different alpha-amylase enzyme formulations at high pH (three different production lots) at five months. Formulation A contains 40% glycerol, 0.1% methyl paraben, 0.2% potassium sorbate, 10 mM sodium citrate, pH 6.5; formulation B contains 50% glycerol, 0.2% potassium sorbate, 10 mM sodium citrate, pH 6.5. Each of three enzyme production lots were formulated into the two different formulations. The samples were stored at 4° C., 25° C., 30° C. and 40° C., respectively.
Figure 7B:
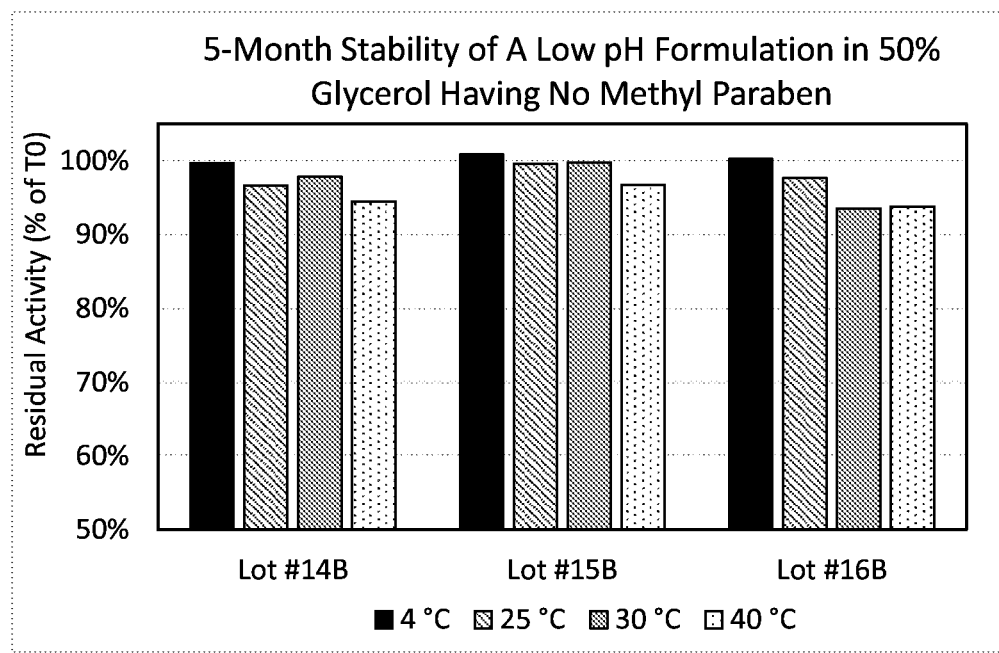

The current alpha-amylase high pH formulation comprises 40% w/v glycerol, 0.1% w/v methyl paraben, pH 10.7. The selection of pH 10.7 was the due to limited solubility of the enzyme at lower pH and the process difficulty in titrating the pH down across a wide range after downstream recovery. The high pH formulation does not provide the necessary product stability because it is unbuffered, pH drift which occurs over time poses a risk for subsequent microbial contamination and commercial losses during bulk shipment, warehouse storage, or product storage at industrial plants. The present disclosure provides a liquid enzyme formulation comprising an alpha-amylase formulation that has a neutral or acidic pH for increased stability and shelf life.

Definitions

The term "liquid enzyme formulation" means to a liquid composition comprising an enzyme. In some embodiments, a liquid enzyme formulation further comprises a buffer, a stabilizer, and a preservative. In some embodiments, the enzyme is an alpha-amylase, a beta-amylase, a glucoamylase, a protease, a phytase, a pullulanase, a cellulase, cellobiohydrolase, a beta-glucosidase, an endoglucanase, a mannanase, a xylanase, or any combination of enzymes thereof.

An enzyme is a biological molecule comprising a sequence of amino acids, wherein the enzyme can catalyze a reaction. Enzyme names are known to those skilled in the art based on the recommendations of the Nomenclature Committee of the International Union of Biochemistry and Molecular Biology (IUBMB). Enzyme names include: an EC (Enzyme Commission) number, recommended name, alternative names (if any), catalytic activity, and other factors. Enzymes are also referred to as a polypeptide, a protein, a peptide, an amino acid sequence, or is identified by a SEQ ID NO. in this disclosure.

An enzyme is "thermostable" if it retains a substantial amount of its activity after a high temperature treatment of at least about 65° C. to about 95° C.; or at a temperature greater than 95° C. In some embodiments, the thermostable enzyme retains at least: 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of its enzymatic activity.

Starch can be any virgin, modified, or degraded starch, or polysaccharide/oligosaccharide. Virgin starches may consist of amylose, amylopectin, or mixtures thereof. Modified starches may comprise oxidized starch, starch esters, or starch ethers.

Types of starch contemplated include virgin starches such as potato starch; wheat starch, corn starch, rice starch, or other grain based starch; or tapioca starch, preferably corn starch. The starches could also be any biomass-containing starch components from plants or agricultural residues. Chemically modified starches may also be used, such as hydroxyethyl or hydroxypropyl starches, or else starches which contain anionic groups, such as phosphate starch, or else cationized starches containing quaternary ammonium groups, preference being given to a degree of substitution DS of 0.01 to 0.2. This degree of substitution DS indicates the number of cationic groups present on average in the starch per glucose unit. Particularly preferred are amphoteric starches, which contain not only quaternary ammonium groups but also anionic groups such as carboxylate and/or phosphate groups, and which may optionally also have undergone chemical modification, having for example been hydroxyalkylated or alkyl-esterified. The starches may be used individually or else in any desired mixtures with one another.

The starches may be present with other hemicelluloses or polysaccharides, such as but not limited to galactomannans, xylans, arabinoxylans, glucuronoxylans, glucomannans, xyloglucans (such as Tamarind seed flour), pectins/pectate, galactans, arabinogalactans. In the case where starch used contains other polysaccharides, it is optional that hemicellulase enzymes or polysaccharide enzymes may be used in combination with the amylase for the preparations of surface starch composition of the present disclosure. In one option, xylanases (for example: Luminase™ PB-100, Luminase™ PB-200) from BASF can be used. In fact hemicellulases, xylanases, cellulases, and other enzymes from any suppler is implied, including from Novozymes, Dyadic, Dupont, and BASF. If the starchy materials contain proteins and fats, protease and lipases may optionally be used in combination with the aforementioned enzymes comprising amylase.

The starch used in the present disclosure, preferably, is a native starch, or a substantially un-modified starch. One example is the Pearl starch from Tate and Lyle. However, the starch used can also be any modified or partially modified starches, as modified by thermal treatment, by thermal-mechanical treatment, by acid hydrolysis, by oxidations, by ester derivatizations, (such as starch acetates, starch phosphates), by ether modifications or hydroxyl-alkyl derivatizations (such as hydroxypropyl starches, hydroxyethyl starches or ethylated starches, hydroxypropyl starch phosphates, carboxymethyl starches, various cationic starches, and previously enzyme modified starches, and pre-gelatinized starches. Common examples include industrial starches from A. E. Staley, Penford (Ingredion), Tate and Lyle, ADM, Cargill, Rasio, Roguette, and Amylum, to name a few.

As used herein, "carbohydrates," "saccharide" or "sugar" refers to a macromolecule consisting of carbon (C), hydrogen (H), and oxygen (O) atoms, usually with a hydrogen: oxygen atom ratio of 2:1 (as in water); in other words, with the empirical formula $C_m(H_2O)_n$ (where m could be different from n). Polysaccharides can have more than one saccharide and are used for the storage of energy. Monosaccharides contain only one saccharide unit, while a disaccharide can contain two saccharide units, or two joined monosaccharides.

A "buffering agent" means a weak acid or base used to maintain the acidity (pH) of a solution near a chosen value after the addition of another acid or base.

A "stabilizer" means a chemical that minimize the instability of an enzyme and therefore maintain its stability. The instability of an enzyme can be due conformational instability, colloidal instability or chemical degradation, which can lead to the loss of enzymatic activity. Examples of stabilizers include but not limited sugars, polyols and salts.

A "preservative" is an agent that kills microorganisms or inhibits their growth, including disinfectants, antiseptics, and antibiotics, etc.

The term "comprising" as used herein is synonymous with "including," "containing," or "characterized by," and is inclusive or open-ended, which means that additional elements not recited or method steps not recited can be within the scope of this disclosure.

It is understood that aspects and embodiments of the invention described herein include "consisting" and/or "consisting essentially of" aspects and embodiments.

Throughout this disclosure, various aspects are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present disclosure will become apparent from the following specification taken in conjunction with the accompanying drawings.

In the following description, numerous specific details are set forth to provide a more thorough understanding of the present disclosure. However, it will be apparent to one of skill in the art that the methods of the present disclosure may be practiced without one or more of these specific details. In other instances, well-known features and procedures well known to those skilled in the art have not been described in order to avoid obscuring the disclosure.

Liquid Enzyme Formulations

Some embodiments disclosed herein provide liquid enzyme formulations comprising an alpha-amylase and a buffering agent, wherein the pH of the enzyme formulation is about pH 6.0-8.0. In some embodiments, the liquid enzyme formulations comprise a stabilizer. In some embodiments, the liquid enzyme formulations comprise a preservative.

An enzyme is a biological molecule comprising a sequence of amino acids, wherein the enzyme can catalyze a reaction. Enzyme names are known to those skilled in the art based on the recommendations of the Nomenclature Committee of the International Union of Biochemistry and Molecular Biology (IUBMB). Enzyme names include: an EC (Enzyme Commission) number, recommended name, alternative names (if any), catalytic activity, and other factors. Enzymes are also known as a polypeptide, a protein, a peptide, an amino acid sequence, or is identified by a SEQ ID NO. In this disclosure, the alternative names for enzyme can be used interchangeably. An "alpha-amylase" is an enzyme that catalyzes the hydrolysis of 1,4-alpha-D-glucosidic linkages to degrade polysaccharides, oligosaccharides, and/or starch into glucose subunits. The enzyme classification for an alpha-amylase is EC 3.2.1.1.

The liquid enzyme formulations disclosed herein may be a pH that is suitable for the stability and maintains the activity of the enzyme contained therein. For example, the pH of the liquid enzyme formulation may be a value that is, is about, is less than, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, or a range that is between any two of the above-mentioned values. In some embodiments, the pH of the liquid enzyme formulation is about pH 6.0-7.5, pH 6.0-7.0, pH 6.0-6.7, or pH 6.3-6.7.

A variety of suitable buffering agents may be used to adjust the pH of the liquid enzyme formulations disclosed herein. For example, the liquid enzyme formulations may comprise a buffering agent selected from the group consisting of: sodium citrate, potassium citrate, citric acid, sodium acetate, acetic acid, sodium phosphate, potassium phosphate, and any combination thereof. In some embodiments, the liquid enzyme formulations comprise a buffering agent that is sodium citrate. The sodium citrate may be included in the liquid enzyme formulations at a concentration that is, is about, is less than, is more than, 0.1% (w/v), 0.2% (w/v), 0.3% (w/v), 0.4% (w/v), 0.5% (w/v), 0.6% (w/v), 0.7% (w/v), 0.8% (w/v), 0.9% (w/v), 1.0% (w/v), 1.1% (w/v), 1.2% (w/v), 1.3% (w/v), 1.4% (w/v), 1.5% (w/v), 1.6% (w/v), 1.7% (w/v), 1.8% (w/v), 1.9% (w/v), 2.0% (w/v), or a range that is between two of any of the above-mentioned values. In some embodiments, the sodium citrate is at a concentration of 0.1-2.0% (w/v) in the liquid enzyme formulation. In some embodiments, the sodium citrate is at a concentration of 0.1-0.6% (w/v) in the liquid enzyme formulation.

A variety of suitable stabilizers may be included in the liquid enzyme formulations disclosed herein. For example, the liquid enzyme formulations may comprise a stabilizer such as sucrose, sorbitol, mannitol, glycerol, trehalose, sodium chloride, sodium sulfate, or any combination thereof. In some embodiments, the liquid enzyme formulations comprise a stabilizer that is glycerol. The glycerol may be included in the liquid enzyme formulations at a concentration that is, is about, is less than, is more than, 30% (w/v), 31% (w/v), 32% (w/v), 33% (w/v), 34% (w/v), 35% (w/v), 36% (w/v), 37% (w/v), 38% (w/v), 39% (w/v), 40% (w/v), 41% (w/v), 42% (w/v), 43% (w/v), 44% (w/v), 45% (w/v), 46% (w/v), 47% (w/v), 48% (w/v), 49% (w/v), 50% (w/v), 51% (w/v), 52% (w/v), 53% (w/v), 54% (w/v), 55% (w/v), 56% (w/v), 57% (w/v), 58% (w/v), 59% (w/v), 60% (w/v), 61% (w/v), 62% (w/v), 63% (w/v), 64% (w/v), 65% (w/v), 66% (w/v), 67% (w/v), 68% (w/v), 69% (w/v), 70% (w/v), 71% (w/v), 72% (w/v), 73% (w/v), 74% (w/v), 75% (w/v), or a range that is between two of any of the above-mentioned values. In some embodiments, the glycerol is at a concentration of 30-75% (w/v) in the liquid enzyme formulation. In some embodiments, the glycerol is at a concentration of 30-70% (w/v) in the liquid enzyme formulation. In some embodiments, the glycerol is at a concentration of 30-65% (w/v) in the liquid enzyme formulation. In some embodiments, the glycerol is at a concentration of 30-50% (w/v) in the liquid enzyme formulation. In some embodiments, the glycerol is at a concentration of 38-42% (w/v) in the liquid enzyme formulation.

The liquid enzyme formulations disclosed herein have improved stability characteristics. For example, the alpha-amylase of the liquid enzyme formulation disclosed herein can retain its activity at a high percentage, at elevated temperatures, for a long period of time, and thus the liquid enzyme formulation has a longer shelf life. "Shelf life" as used herein refers to how long the liquid enzyme product can be stored at a particular temperature before it begins to lose its enzymatic activity. In some embodiments, the alpha-amylase retains at least 50%, 60%, 70%, 80%, 90%, 95%, or more, of its activity at a temperature, such as 4-40° C. In some embodiments, the alpha-amylase retains at least 50%, 60%, 70%, 80%, 90%, 95%, or more, of its activity at a temperature of 25-30° C. In some embodiments, the alpha-amylase retains at least 50%, 60%, 70%, 80%, 90%, 95%, or more, of its activity for 1 year. In some embodiments, the alpha-amylase has a shelf life of at least 2 months, 3 months, 4 months, 5 months, 6 months, 7 months, 8 months, 9 months, 10 months, 11 months, 1 year, or more. In some embodiments, the alpha-amylase has a shelf life of at least 2 months, 3 months, 4 months, 5 months, 6 months, 7 months, 8 months, 9 months, 10 months, 11 months, 1 year, or more, at 25° C. In some embodiments, the alpha-amylase has a shelf life of at least 2 months, 3 months, 4 months, 5 months, 6 months, 7 months, 8 months, 9 months, 10 months, 11 months, 1 year, or more, at 37° C.

As disclosed herein, the liquid enzyme formulations may comprise a variety of preservatives, such as potassium sorbate, sodium sorbate, sorbic acid, sodium benzoate, benzoic acid, methyl paraben, calcium propionate, sodium propionate, ammonium propionate, propionic acid, or any combination thereof. In some embodiments, the liquid enzyme formulations disclosed herein comprise no preservative. In some embodiments, the liquid enzyme formulations disclosed herein comprise only one preservative, such as potassium sorbate. In some embodiments, the liquid enzyme formulations disclosed herein comprise at least two preservatives, such as methyl paraben and potassium sorbate. Methyl paraben may be included in the liquid enzyme formulations at a concentration that is, is about, is less than, is more than, 0.00% (w/v), 0.01% (w/v), 0.02% (w/v), 0.03% (w/v), 0.04% (w/v), 0.05% (w/v), 0.06% (w/v), 0.07% (w/v), 0.08% (w/v), 0.09% (w/v), 0.1% (w/v), 0.2% (w/v), 0.3% (w/v), or a range that is between two of any of the above-mentioned values. In some embodiments, the methyl paraben is at a concentration of 0.05-0.3% (w/v) in the liquid enzyme formulation. In some embodiments, the methyl paraben is at a concentration of 0.1% (w/v) in the liquid enzyme formulation. The potassium sorbate may be included in the liquid enzyme formulations at a concentration that is, is about, is less than, is more than, 0.1% (w/v), 0.2% (w/v), 0.3% (w/v), 0.4% (w/v), 0.5% (w/v), or a range that is between two of any of the above-mentioned values. In some embodiments, the potassium sorbate is at a concentration of 0.1-0.5% (w/v) in the liquid enzyme formulation. In some embodiments, the potassium sorbate is at a concentration of 0.2% (w/v) in the liquid enzyme formulation.

In some embodiments, the liquid enzyme formulations may comprise sodium citrate at a concentration of 0.1-2.0% (w/v), glycerol at a concentration of 30-75% (w/v), methyl paraben at a concentration of 0.0-0.3% (w/v), and potassium sorbate at a concentration of 0.1-0.5% (w/v), in the liquid enzyme formulation. In some embodiments, the liquid enzyme formulations may comprise sodium citrate at a concentration of 0.1-0.6% (w/v), glycerol at a concentration of 38-50% (w/v), methyl paraben at a concentration of 0.1%

(w/v), and potassium sorbate at a concentration of 0.2% (w/v), in the liquid enzyme formulation.

Some embodiments disclosed herein provide polypeptides having amylase activities and their uses in the production of a food product, a biofuel, a cleaning product, an animal feed, or a paper pulp, etc., and enhanced oil recovery, etc. In some embodiments, the amylase can be a thermostable alpha amylase, for example a thermostable alpha amylase from bacteria (e.g., *Bacillus*) or fungi, or any combination (mixture) of enzymes thereof.

In some embodiments, the alpha amylase comprises or has an amino acid sequence set forth in one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

In some embodiments, the alpha amylase is variant of the parent alpha amylase that comprises or has an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence set forth in any of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14, wherein the variant has alpha amylase activity.

In some embodiments, the alpha amylase is one of the alpha amylase disclosed in the following patent applications: WO2014007921, WO2011017093, WO2010074999, WO1994019454, WO2010008841, WO2011080352, WO2011080354, WO2011082429, WO199744361, WO2002068589, WO202068597, WO2002092802, WO2003083054, WO2004091544, WO2009020459, WO2013116175, WO2013148163, WO2008080093, and WO2003018766. The contents of these patent applications are hereby incorporated by reference in their entireties.

In some embodiments, the alpha amylase is FUELZYME™ (BASF Enzymes LLC, San Diego, CA). Other non-limiting examples of the amylases suitable for use in the methods and compositions disclosed herein include: LpHera® from Novozymes; SPEZYME® XTRA, SPEZYME® CL, SPEZYME® Alpha, SPEZYME® RSL, SPEZYME® FRED, SPEZYME® LT 300, AmyS, AmyL, BAN®480L, Liquozyme® Supra, Liquozyme® SCDS, MAX-LIFE™ P100, Maltogenase L, CLARASE® L, Liquozyme® SC, Termamyl® SC, Veretase, Liqozyme® SC4x, Liquozyme® Supra 2.8, Liquozyme® supra 2, Liquozyme® X, Termamyl® 120L, SPEZYME® ALPHA, Clearflow® AA, Optitherm™, Takatherm™, Keistase™, Avantec, and SZM XT-20.

In addition to the alpha amylase, the liquid enzyme formulations disclosed herein can include one or more additional enzymes. In some embodiments, the liquid enzyme formulation comprises a second enzyme. In some embodiments, the second enzyme is selected from the group consisting of an alpha-amylase, a beta-amylase, a glucoamylase, a protease, a phytase, a pullulanase, a cellulase, a cellobiohydrolase, a beta-glucosidase, an endoglucanase, a mannanase, and any combination thereof. In some embodiments, the liquid enzyme formulation comprises two or more enzymes. For example, the liquid enzyme formulation can contain the alpha amylase, a second enzyme, and a third enzyme. The third enzyme can be, for example, an alpha-amylase, a beta-amylase, a glucoamylase, a protease, a phytase, a pullulanase, a cellulase, a cellobiohydrolase, a beta-glucosidase, an endoglucanase, a mannanase, or any combination thereof.

In some embodiments, the liquid enzyme formulations comprise a cellulase or a variant thereof. In some embodiments, the cellulase is any of the cellulases derived from hyperthermophilic bacteria and/or non-naturally occurring variants thereof described in PCT publication WO 2009/020459 (the entire disclosure of which is incorporated herein by reference). The cellulase enzyme can be PYROLASE, SZM_XC, SPIRIZYME, or OPTIMASH.

In another embodiment, the additional enzyme can be a phytase (EC 3.1.3.8; 3.1.3.26; and 3.1.1.72). Examples of a commercially available phytase can be FUELTASE™, NATURPHOS™, PHYZYME™, PHYTAVERSE™, OR OMPTIMASH™.

In another embodiment, the additional enzyme ca be a protease. Examples of commercially available protease include: Deltazymt, Fermgent, and SZM AP-1.

In another embodiment, the additional enzyme can be a glucoamylase. Examples of commercial glucoamylase enzymes are DELTAZYM®, SPIRIZYME®, DISTALASE®, OPTIMASH™, STARGEn®, and GLUCOAMYL.

In another embodiment, the additional enzyme can be a xylanase. Examples of commercially xylanase enzymes include: Xylathin™, Optimash In some embodiments, the liquid enzyme formulations comprise a beta-glucosidase or a variant thereof.

In some embodiments, the beta-glucosidase can be a commercially available product, or any mixture thereof.

In some embodiments, the beta-glucosidase can be any of the beta-glucosidases from *Thermotoga maritima* (BGT), *Phanerochaete chrysosporium* (BGP), or *Aspergillus niger* (BG) (Sigma, St. Louis, MO).

Lipases (E.C. 3.1.1.3), Phospholipase A1 (E.C. 3.1.1.32), Phospholipase A2 (E.C. 3.1.1.4), Phospholipase C (E.C. 3.1.4.3), Phospholipase D (E.C. 3.1.4.4); Galactolipase (E.C. 3.1.1.26), are hydrolytic enzymes that are known to cleave ester bonds in lipids. Lipases include phospholipases, triacylglycerol lipases, and galactolipases. Lipases have been identified from plants; mammals; and microorganisms including but not limited to: *Pseudomonas, Vibrio, Acinetobacter, Burkholderia*, Chromobacterium, Cutinase from *Fusarium solani* (FSC), *Candida antarctica* A (CalA), *Rhizopus oryzae* (ROL), *Thermomyces lanuginosus* (TLL), *Rhizomucor miehei* (RML), *Aspergillus Niger, Fusarium heterosporum, Fusarium oxysporum, Fusarium culmorum* lipases.

In addition, many lipases, phospholipases, and galactolipases have been disclosed in patents and published patent applications including, but not limited to: WO1993/000924, WO2003/035878, WO2003/089620, WO2005/032496, WO2005/086900, WO2006/031699, WO2008/036863, and WO2011/046812.

Commercial lipases used for process fats include: LIPOPAN™, NOOPAZYME, LIPOPAN MAX, LIPOPAN Xtra (available from Novozymes); PANAMORE, CAKEZYME, and BAKEZYME (available from DSM); and GRINDAMYL EXEL 16, GRINDAMYL POWERBAKE, and TS-E 861 (available from Dupont/Danisco).

A "parent" sequence (of a parent protein or enzyme, also called "parent enzyme") is the starting sequence for introduction of changes (e.g. by introducing one or more amino acid substitutions, insertions, deletions, or a combination thereof) to the sequence, resulting in "variants" of the parent sequences. The term parent enzyme (or parent sequence) includes 1. wild-type enzymes (sequences) and
2. Synthetically generated sequences (enzymes) which are used as starting sequences for introduction of (further) changes.

"Enzyme variants" or "sequence variants" or "variant enzymes" refers to an enzyme that differs from its parent enzyme in its amino acid sequence to a certain extent. If not indicated otherwise, variant enzyme "having enzymatic activity" means that this variant enzyme has the same type of enzymatic activity as the respective parent enzyme.

In an embodiment, the variant polypeptide having an amino acid substitution can be a conservative amino acid substitution. A "conservative amino acid substitution" means replacement of one amino acid residue in an amino acid sequence with a different amino acid residue having a similar property at the same position compared to the parent amino acid sequence. Some examples of a conservative amino acid substitution include but are not limited to replacing a positively charged amino acid residue with a different positively charged amino acid residue; replacing a polar amino acid residue with a different polar amino acid residue; replacing a non-polar amino acid residue with a different non-polar amino acid residue, replacing a basic amino acid residue with a different basic amino acid residue, or replacing an aromatic amino acid residue with a different aromatic amino acid residue.

WIPO Standard ST.25 (1998) provides that the amino acid residues should be represented in the sequence listing using the following three-letter symbols with the first letter as a capital. The table below provides an overview of the amino acid identifiers as well as the corresponding DNA codons that encode the amino acid using the standard genetic standard. The DNA codons that encode amino acid residues can be different depending organism that is used and slightly different tables for translation of the genetic code may apply. A compilation of such non-standard code translation tables is maintained at the NCBI. For reference see e.g. https://www.ncbi.nlm.nih.gov/Taxonomy/Utils/wprintgc.cgi.

| Amino Acids | | | |
|---|---|---|---|
| Name | 3 letter code | 1 letter code | DNA codons |
| Alanine | Ala | A | GCA, GCC, GCG, GCT |
| Arginine | Arg | R | AGA, AGG, CGA, CGC, CGG, CGT |
| Asparagine | Asn | N | AAC, AAT |
| Aspartic acid; (Aspartate) | Asp | D | GAC, GAT |
| Cysteine | Cys | C | TGC, TGT |
| Glutamic acid; (Glutamate) | Glu | E | GAA, GAG |
| Glutamine | Gln | Q | CAA, CAG |
| Glycine | Gly | G | GGA, GGC, GGG, GGT |
| Histidine | His | H | CAC, CAT |
| Isoleucine | Ile | I | ATA, ATC, ATT |
| Leucine | Leu | L | CTA, CTC, CTG, CTT, TTA, TTG |
| Lysine | Lys | K | AAA, AAG |
| Methionine | Met | M | ATG |
| Phenylalanine | Phe | F | TTC, TTT |
| Proline | Pro | P | CCA, CCC, CCG, CCT |
| Serine | Ser | S | AGC, AGT, TCA, TCC, TCG, TCT |
| Threonine | Thr | T | ACA, ACC, ACG, ACT |
| Tryptophan | Trp | W | TGG |

-continued

| Amino Acids | | | |
|---|---|---|---|
| Name | 3 letter code | 1 letter code | DNA codons |
| Tyrosine | Tyr | Y | TAC, TAT |
| Valine | Val | V | GTA, GTC, GTG, GTT |

In a further embodiment, the variant polypeptide having lipase activity is a "mature polypeptide." A mature polypeptide means an enzyme in its final form including any post-translational modifications, glycosylation, phosphorylation, truncation, N-terminal modifications, C-terminal modifications, signal sequence deletion. A mature polypeptide can vary depending upon the expression system, vector, promoter, and/or production process.

"Sequence Identity," "% sequence identity." "% identity," or "Sequence alignment" means a comparison of a first amino acid sequence to a second amino acid sequence, or a comparison of a first nucleic acid sequence to a second nucleic acid sequence and is calculated as a percentage based on the comparison. The result of this calculation can be described as "percent identical" or "percent ID."

Generally, a sequence alignment can be used to calculate the sequence identity by one of two different approaches. In the first approach, both, mismatches at a single position and gaps at a single position are counted as non-identical positions in final sequence identity calculation. In the second approach, mismatches at a single position are counted as non-identical positions in final sequence identity calculation; however, gaps at a single position are not counted (ignored) as non-identical positions in final sequence identity calculation. In other words, in the second approach gaps are ignored in final sequence identity calculation. The differences between these two approaches, counting gaps as non-identical positions vs ignoring gaps, at a single position can lead to variability in sequence identity value between two sequences.

In an embodiment of this disclosure, sequence identity is determined by a program, which produces an alignment, and calculates identity counting both mismatches at a single position and gaps at a single position as non-identical positions in final sequence identity calculation. For example program Needle (EMBOS), which has implemented the algorithm of Needleman and Wunsch (Needleman and Wunsch, 1970, J. Mol. Biol. 48: 443-453), and which calculates sequence identity by first producing an alignment between a first sequence and a second sequence, then counting the number of identical positions over the length of the alignment, then dividing the number of identical residues by the length of an alignment, then multiplying this number by 100 to generate the % sequence identity [% sequence identity=(# of Identical residues/length of alignment)×100)].

In another embodiment of this disclosure, sequence identity can be calculated from a pairwise alignment showing both sequences over the full length, so showing the first sequence and the second sequence in their full length ("Global sequence identity"). For example, program Needle (EMBOSS) produces such alignments; % sequence identity=(# of identical residues/length of alignment)×100)].

In another embodiment of this disclosure, sequence identity can be calculated from a pairwise alignment showing only a local region of the first sequence or the second sequence ("Local Identity"). For example, program Blast (NCBI) produces such alignments; % sequence identity=(# of Identical residues/length of alignment)×100)].

In a preferred embodiment, a sequence alignment is calculated with mismatches at a single position are counted as non-identical positions in final sequence identity calculation; however, gaps at a single position are not counted (ignored) as non-identical positions in final sequence identity calculation. The sequence alignment is generated by using the algorithm of Needleman and Wunsch (J. Mol. Biol. (1979) 48, p. 443-453). Preferably, the program "NEEDLE" (The European Molecular Biology Open Software Suite (EMBOSS)) is used for the purposes of the current invention, with using the programs default parameter (gap open=10.0, gap extend=0.5 and matrix=EBLOSUM62). Then, a sequence identity can be calculated from the alignment showing both sequences over the full length, so showing the first sequence and the second sequence in their full length ("Global sequence identity"). For example, % sequence identity=(# of identical residues/length of alignment)×100)].

Methods of Making a Liquid Enzyme Formulation

Some embodiments disclosed herein provide methods of making a liquid enzyme formulation, wherein the methods comprise titrating the pH of the liquid enzyme formulation to a range of pH 6.0-8.0. In some embodiments, the methods comprise a step of providing a composition comprising an alpha-amylase, wherein the composition has a pH of about pH 8.0-10.5. In some embodiments, the methods comprise a step of adding a stabilizer to the composition comprising alpha-amylase to obtain a liquid enzyme formulation.

A non-limiting example of the method 100 of making a liquid enzyme formulation in accordance with the embodiments disclosed herein is illustrated in the flow diagram shown in FIG. 1. As illustrated in FIG. 1, the method 100 can include one or more functions, operations or actions as illustrated by one or more operations 110-160.

Method 100 can begin at optional operation 110, "Obtaining recovery material." Recovery, often also referred to as downstream recovery, is a process of separating enzyme in the fermentation broth from the expression organism, and the enzyme is potentially further concentrated, purified, refined, washed or buffered exchanged in the solution. Recovery material, sometimes also referred to as enzyme concentrate, contains enzyme in concentrated solution after the recovery process but before the formulation steps. Operation 110 can be followed by operation 120, "Pre-formulation." In this step, a stabilizer may be added to the recovery material, to initially stabilize the enzyme, prior to the additions of other formulation ingredients and additional adjustments to the final formulated product. Operation 120 can be followed by optional operation 130, "Adding preservative to pre-formulation mixture." Operation 130 can be followed by optional operation 140, "Small volume pH titration test." In this test, a stock solution of concentrated acidic buffer at a particular pH is added and mixed to the pre-formulation mixture incrementally, and the pH of the solution is measured. When the pH of the solution reaches the target range of the final formulation, the volume of the stock buffer solution required is recorded. An additional buffer stock solution at a lower pH may be required to repeat the titration test if too much buffer stock volume is used in the initial test. The purpose of this titration test is to determine the precise pH and volume of an acidic buffer stock solution required so that the final formulation solution reaches target pH range within the concentration range of the buffer reagent in the final formulation. In some embodiments, no additional strong acid is used for the pH titration. In some embodiments, a set volume of the buffer stock solution is added to the pre-formulation mixture, and then a strong acid is used to adjust the final pH to the formulation target in the titration test. The exact volumes of the buffer stock solution and acid used are recorded. Operation 140 can be followed by operation 150 "Titrating pH of liquid enzyme formulation." This step may be carried out based on the result from Operation 140. The volume and pH requirements of the acidic buffer stock solution and the strong acid are scaled up to the entire production volume. Operation 150 can be followed by optional operation 160, "Obtaining final formulated liquid product and packaging."

In FIG. 1, operations 110-160 are illustrated as being performed sequentially with operation 110 first and operation 160 last. It will be appreciated, however, that these operations can be combined and/or divided into additional or different operations as appropriate to suit particular embodiments. For example, additional operations can be added before, during or after one or more operations 110-160. In some embodiments, one or more of the operations can be performed at about the same time. In some embodiments, the method only consists of operations 120 and 150, but not any other operations. In some embodiments, the method consists essentially of operations 120 and 150. In some embodiments, the method only consists of operations 120, 150 and one of operations 110, 130, 140 and 160, but not any other operations. In some embodiments, the method only consists of operations 120, 150 and two of operations 110, 130, 140 and 160, but not any other operations. In some embodiments, the method only consists of operations 120, 150 and one or more of operations 110, 130, 140 and 160, but not any other operations.

At optional operation 110, "Obtaining recovery material," the recovery material is not particularly limited and can be any composition comprising an alpha-amylase. The pH of the recovery material is not particularly limited. For example, the composition comprising an alpha-amylase may have a pH value that is, is about, is less than, is more than, pH 8.0, pH 8.1, pH 8.2, pH 8.3, pH 8.4, pH 8.5, pH 8.6, pH 8.7, pH 8.8, pH 8.9, pH 9.0, pH 9.1, pH 9.2, pH 9.3, pH 9.4, pH 9.5, pH 9.6, pH 9.7, pH 9.8, pH 9.9, pH 10.0, pH 10.1, pH 10.2, pH 10.3, pH 10.4, pH 10.5, or a range that is between any two of the above-mentioned values. In some embodiments, the pH of the composition comprising an alpha-amylase may be adjusted to pH 10.0 if needed. In some embodiments, the pH of the composition comprising an alpha-amylase is about pH 8.0-10.5. In some embodiments, the composition comprising an alpha-amylase may have an enzyme activity, e.g., alpha-amylase activity that is at least 300,000 MWU/g (Modified Wohlgemuth Units). In some embodiments, the composition comprising an alpha-amylase may have an enzyme concentration, e.g., alpha-amylase, that is about 300,000-400,000 MWU/g.

At operation 120, "Pre-formulation," a variety of stabilizers may be added to the composition comprising an alpha-amylase. For example, a stabilizer such as sucrose, sorbitol, mannitol, glycerol, trehalose, sodium chloride, sodium sulfate, or any combination thereof, may be added to the composition comprising an alpha-amylase. In some embodiments, glycerol is added to the composition comprising an alpha-amylase as stabilizer. The glycerol may be added to the composition comprising an alpha-amylase to a final concentration that is, is about, is less than, is more than, 30% (w/v), 31% (w/v), 32% (w/v), 33% (w/v), 34% (w/v), 35% (w/v), 36% (w/v), 37% (w/v), 38% (w/v), 39% (w/v), 40% (w/v), 41% (w/v), 42% (w/v), 43% (w/v), 44% (w/v), 45% (w/v), 46% (w/v), 47% (w/v), 48% (w/v), 49% (w/v), 50% (w/v), 51% (w/v), 52% (w/v), 53% (w/v), 54% (w/v), 55% (w/v), 56% (w/v), 57% (w/v), 58% (w/v), 59% (w/v), 60% (w/v), 61% (w/v), 62% (w/v), 63% (w/v), 64% (w/v), 65% (w/v), 66% (w/v), 67% (w/v), 68% (w/v), 69% (w/v), 70% (w/v), 71% (w/v), 72% (w/v), 73% (w/v), 74% (w/v), 75% (w/v), or a range that is between two of any of the above-mentioned values. In some embodiments, the glycerol is added to the composition comprising an alpha-amylase to a final concentration of 30-50% (w/v). In some embodiments, the glycerol is added to the composition comprising an alpha-amylase to a final concentration of 38-42% (w/v).

At optional operation 130, "Adding preservative to pre-formulation mixture," a variety of preservatives may be added. A preservative such as a potassium sorbate, sodium sorbate, a sorbic acid, a sodium benzoate, a benzoic acid, a methyl paraben, a calcium propionate, a sodium propionate, an ammonium propionate, a propionic acid, or any combination thereof, may be added to the pre-formulation mixture. In some embodiments, no preservative is added to the pre-formulation mixture. In some embodiments, one preservative, added to the pre-formulation mixture. In another embodiment, the one preservative added to the pre-formulation mixture is potassium sorbate. In some embodiments, at least two preservatives, such as methyl paraben and potassium sorbate, can be added to the pre-formulation mixture. The methyl paraben can be added to the pre-formulation mixture to a final concentration that is, is about, is less than, is more than, 0.00% (w/v), 0.01% (w/v), 0.02% (w/v), 0.03% (w/v), 0.04% (w/v), 0.05% (w/v), 0.06% (w/v), 0.07% (w/v), 0.08% (w/v), 0.09% (w/v), 0.1% (w/v), 0.2% (w/v), 0.3% (w/v), or a range that is between two of any of the above-mentioned values. In some embodiments, the methyl paraben may be added to the pre-formulation mixture to a final concentration of 0.05-0.3% (w/v). In some embodiments, the methyl paraben may be added to the pre-formulation mixture to a final concentration of 0.1% (w/v). The potassium sorbate may be added to the pre-formulation mixture to a final concentration that is, is about, is less than, is more than, 0.1% (w/v), 0.2% (w/v), 0.3% (w/v), 0.4% (w/v), 0.5% (w/v), or a range that is between two of any of the above-mentioned values. In some embodiments, the potassium sorbate is added to the pre-formulation mixture to a final concentration of 0.1-0.5% (w/v). In some embodiments, the potassium sorbate is added to the pre-formulation mixture to a final concentration of 0.2% (w/v).

At optional operation 140, "Small volume pH titration test," the pH of the acidic buffer stock solution may be a value that is, is about, is less than, is more than, pH 2.5, 3.0, 3.5, 4.0, 4.5, 5.0, 5.5, 6.0, 6.5, or a range that is between any two of the above-mentioned values. In some embodiments, the pH of the acidic buffer stock solution is about pH 4.0. In other embodiments, the pH of the acidic buffer stock solution is about pH 3.5. The concentration of the buffer stock solution may be a value that is, is about, is less than, is more than, 5% (w/v), 10% (w/v), 15% (w/v), 20% (w/v), 25% (w/v), 30% (w/v), 35% (w/v), 40% (w/v), or a range that is between any two of the above-mentioned values. A variety of suitable strong acid may be used to titrate the pH in the small volume titration test. For example, the pH during the titration test may be titrated using an acid selected from the group consisting of: citric acid, acetic acid, sulfuric acid, phosphoric acid, hydrochloric acid, and any combination thereof. Small volume in this test refers to a sample volume that is convenient and consistent for lab scale titration, solution mixing and pH measurement, for example, 100 milliliters to 1 liter.

At operation 150, "Titrating pH of liquid enzyme formulation," the pH of the liquid enzyme formulation can vary. For example, the pH of the liquid enzyme formulation may be a value that is, is about, is less than, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, or a range that is between any two of the above-mentioned values. In some embodiments, the pH of the liquid enzyme formulation is about pH 6.3-6.7.

A variety of suitable buffering agents may be used to titrate the pH of the liquid enzyme formulations disclosed herein. For example, the pH of the liquid enzyme formulations may be titrated using a buffering agent selected from the group consisting of: sodium citrate, potassium citrate, citric acid, sodium acetate, acetic acid, sodium phosphate, potassium phosphate, and any combination thereof. In preferred embodiments, the pH of the liquid enzyme formulations may be titrated using a buffering agent that is sodium citrate. The sodium citrate may be added to the liquid enzyme formulations to a final concentration that is, is about, is less than, is more than, 0.1% (w/v), 0.2% (w/v), 0.3% (w/v), 0.4% (w/v), 0.5% (w/v), 0.6% (w/v), 0.7% (w/v), 0.8% (w/v), 0.9% (w/v), 1.0% (w/v), 1.1% (w/v), 1.2% (w/v), 1.3% (w/v), 1.4% (w/v), 1.5% (w/v), 1.6% (w/v), 1.7% (w/v), 1.8% (w/v), 1.9% (w/v), 2.0% (w/v), or a range that is between two of any of the above-mentioned values. In some embodiments, the sodium citrate may be added to the liquid enzyme formulations to a final concentration of 0.1-2.0% (w/v). In some embodiments, the sodium citrate may be added to the liquid enzyme formulations to a final concentration of 0.1-0.6% (w/v). In some embodiments, a buffered sodium citrate stock solution may be used, instead of a strong acid solution (including citric acid), in order to avoid enzyme precipitation. In some embodiments, the buffered sodium citrate stock solution has a pH of about 3.0-5.0.

At optional operation 160, "Obtaining final formulated liquid product and packaging," the liquid enzyme formulation after pH adjustment is obtained.

Uses of a Liquid Enzyme Formulation

The liquid enzyme formulations disclosed herein can be used in any applications in which the alpha amylase is suitable. Some embodiments disclosed herein provide uses of a liquid enzyme formulation comprising an alpha-amylase, a buffering agent, a stabilizer and a preservative, wherein the pH of the liquid enzyme formulation is about pH 6.0-8.0 for hydrolyzing a starch. In some embodiments, the liquid enzyme formulation is used for the production of a food product, a biofuel, a cleaning product, an animal feed, or a paper pulp. In some embodiments, the liquid enzyme formulation is used for enhanced oil recovery.

Figure 8:
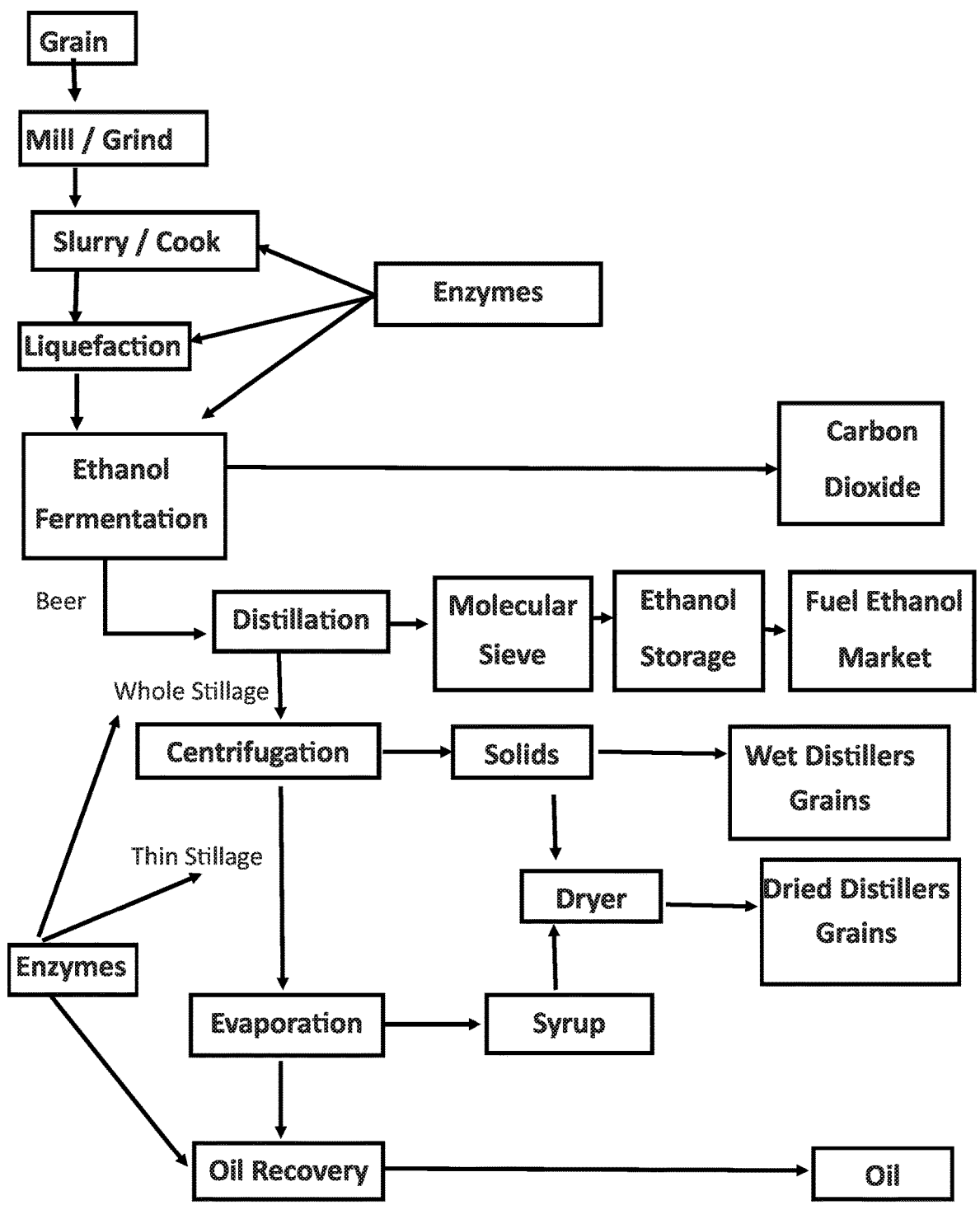
FIG. 8, shows an example of the ethanol production process.

An "ethanol production process" is described in FIG. 8, which includes grain processing, first generation ethanol production from corn to ethanol; generation 1.5 ethanol production which includes a combination the first-generation corn ethanol production process and cellulosic ethanol production; and second generation cellulosic ethanol production of biofuels.

"Grain" includes a composition comprising corn and can also be any biomass feedstock sources such as wheat, or sugarcane.

The biomass conversion process generates various products for food, alcohol, nutraceutical, personal care products, starches, and other bio-based products.

EXAMPLES

The examples which follow illustrate aspects of the present disclosure. The percentages in the examples are by weight, unless otherwise stated.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1

Preparation of Buffered Low pH Alpha-Amylase Formulation with Strong Acid Titration Recovery material representing product which would be formulated ("concentrate") was obtained and alpha-amylase enzyme activity (MWU/g; MWU, Modified Wohlgemuth Units), pH, and microbial load (CFU/mL; CFU, colony forming units) were determined upon receipt. pH of the concentrate was adjusted to 10.7 if needed. Activity target for the concentrate was ≥300,000 MWU/g (necessary to meet pre-formulation target of 185,000 MWU/g after addition of 40% w/v glycerol).

Pre-formulation mixture was prepared by combining concentrate, 40% w/v glycerol, and DI-water. pH of the pre-formulation mixture was adjusted to 10.7 with 1N NaOH. Activity target at pre-formulation step was 185,000 MWU/g.

Pre-formulation mixture was optionally pasteurized by heating at 70° C. for 1 hour.

To prepare a low pH formulation, 100× citrate phosphate buffer stock solution (326 mM citric acid, 436 mM $Na_2HPO_4$, 800 mM NaOH, pH 6.5) was added to the mixture to 1× final concentration (3.3 mM citric acid, 4.4 mM $Na_2HPO_4$, 8 mM NaOH). Following buffer addition, preservatives were added to 0.1% w/v final concentration each (methyl paraben, added from 25% w/v stock in 100% ethanol; potassium sorbate, added from 25% w/v stock solution in DI water). Additional glycerol was added to the final formulation solution to achieve 40% w/v glycerol concentration. The final pH of the formulation mixture was adjusted to 6.5 with 12% citric acid. To prepare a high pH formulation (unbuffered, pH 10.7), 0.1% w/v methyl paraben was added to the pre-formulation mixture, and pH was adjusted to 10.7 with 1N NaOH. Additional glycerol was added to the final formulation solution to achieve 40% w/v glycerol concentration. Activity target for the final formulation was 160,000 MWU/g.

In some embodiments, the formulation mixture may be aliquoted in sterile plastic containers (bottles or tubes) and stored at designated temperatures where stability was monitored (−20° C., 5° C., 22° C., 30° C., and 37° C.).

Enzyme activity was monitored using MWU assay, protein quality and integrity were monitored using HPLC/Reverse phase and SDS PAGE, pH and microbial stability were monitored monthly for minimum of three months.

pH stability was determined by taking an aliquot of formulated material stored at each designated temperature and determining the pH of the solution. Microbial stability was determined by taking an aliquot of formulated material stored at each designated temperature and plating 200 μl on 20 mm TSA plates (tryptic soy agar, DIFCO Laboratories).

Example 2

Preparation of Buffered Low pH Alpha-Amylase Formulation Containing Methyl Paraben without Strong Acid Titration Recovery material representing product which would be formulated ("concentrate") was obtained and enzyme (alpha-amylase) activity (MWU/g; MWU, Modified Wohlgemuth Units), pH, and microbial load (CFU/mL; CFU, colony forming units) were determined upon receipt. Activity target for the concentrate was ≥300,000 MWU/g (necessary to meet pre-formulation target of 185,000 MWU/g after addition of 40% w/v glycerol).

Pre-formulation mixture was prepared by combining concentrate, 40% w/v glycerol, and DI-water. Activity target at pre-formulation step was 185,000 MWU/g.

Pre-formulation mixture was optionally pasteurized by heating at 70° C. for 1 hour.

To prepare a low pH formulation, preservatives were added to the pre-formulation mixture to final concentrations of 0.1% w/v for methyl paraben (added from 25% w/v stock solution in 100% ethanol or 10% w/v stock solution from mono propylene glycol) and 0.2% potassium sorbate (added from 25% w/v stock solution in DI water). One kilogram of this pre-formulation mixture with preservatives was retrieved. Small volumes of 1 molar sodium citrate buffer stock solution at pH 4.0 were added to the mixture at 1 gram step increment. The mixture was thoroughly mixed and pH was constantly measured. When the mixture pH reached 6.5, the titration test was stopped and the total amount of sodium citrate stock solution added was recorded. Based on the 1-kilogram pH titration test, the amount of buffer stock solution needed for formulating the entire production volume was calculated. This volume of 1 molar sodium citrate buffer stock solution at pH 4.0 was then added to the entire pre-formulation mixture with preservatives. Additional glycerol was added to the final formulation solution to achieve 40% w/v glycerol concentration. The pH target of the final formulation mixture was 6.5. If additional pH adjustment was needed, 1 molar sodium citrate buffer stock solution at pH 4.0 or 10% sodium hydroxide would be used. Activity target for the final formulation was 160,000 MWU/g.

The formulation mixture was aliquoted in sterile plastic containers (bottles or tubes) and stored at designated temperatures where stability was monitored (−20° C., 4° C., 25° C., and 40° C.).

Enzyme activity was monitored using MWU assay, protein quality and integrity were monitored using HPLC/Reverse phase and SDS PAGE, pH and microbial stability were monitored monthly for minimum of three months.

pH stability was determined by taking an aliquot of formulated material stored at each designated temperature and determining the pH of the solution. Microbial stability was determined by taking an aliquot of formulated material stored at each designated temperature and plating 200 μl on 20 mm TSA plates (tryptic soy agar, DIFCO Laboratories).

Example 3

Preparation of Buffered Low pH Alpha-Amylase Formulation Containing No Methyl Paraben without Strong Acid Titration Recovery material representing product which would be formulated ("concentrate") was obtained and enzyme (alpha-amylase) activity (MWU/g; MWU, Modified Wohlgemuth Units), pH, and microbial load (CFU/mL; CFU, colony forming units) were determined upon receipt. Activity target for the concentrate was ≥325,000 MWU/g (necessary to meet pre-formulation target of 200,000 MWU/g after addition of 40% w/v glycerol).

Pre-formulation mixture was prepared by combining concentrate, 40% w/v glycerol, and DI-water. Activity target at pre-formulation step was 200,000 MWU/g.

Pre-formulation mixture was optionally pasteurized by heating at 70° C. for 1 hour.

To prepare a low pH formulation, a preservative was added to the pre-formulation mixture to final concentrations of 0.2% potassium sorbate (added from 25% w/v stock solution in DI water). One kilogram of this pre-formulation mixture with preservative was retrieved. Small volumes of 1 molar sodium citrate buffer stock solution at pH 4.0 were added to the mixture at 1 gram step increment. The mixture was thoroughly mixed and pH was constantly measured. When the mixture pH reached 6.5, the titration test was stopped and the total amount of sodium citrate stock solution added was recorded. Based on the 1-kilogram pH titration test, the amount of buffer stock solution needed for formulating the entire production volume was calculated. This volume of 1 molar sodium citrate buffer stock solution at pH 4.0 was then added to the entire pre-formulation mixture with preservative. Additional glycerol was added to the final formulation solution to achieve 50% w/v glycerol concentration. The pH target of the final formulation mixture was 6.5. If additional pH adjustment was needed, 1 molar sodium citrate buffer stock solution at pH 4.0 or 10% sodium hydroxide would be used. Activity target for the final formulation was 160,000 MWU/g.

The formulation mixture was aliquoted in sterile plastic containers (bottles or tubes) and stored at designated temperatures where stability was monitored (−20° C., 4° C., 25° C., and 40° C.).

Enzyme activity was monitored using MWU assay, protein quality and integrity were monitored using HPLC/Reverse phase and SDS PAGE, pH and microbial stability were monitored monthly for minimum of three months.

pH stability was determined by taking an aliquot of formulated material stored at each designated temperature and determining the pH of the solution. Microbial stability was determined by taking an aliquot of formulated material stored at each designated temperature and plating 200 µl on 20 mm TSA plates (tryptic soy agar, DIFCO Laboratories).

Example 4

Viscosity Reduction with Alpha Amylase and a Composition Comprising an Alpha Amylase Alpha amylases of this invention and the liquid formulation comprising an enzyme were added to whole stillage for 1-24 hours and were added in the amount of 0.005 gm/100 gm of whole stillage solids, which is considered a 1.0× loading. The whole stillage was obtained from a dry grind, corn ethanol biorefinery. The viscosity of the samples was measured by a Brookfield Viscometer at various times within a 1-4 hour time range after the alpha amylase was added. The viscosity of the samples were evaluated and plotted over time.

Example 5

Oil Yield with Alpha Amylase and a Composition Comprising an Alpha Amylase

Alpha amylases of this invention and the liquid formulation comprising an alpha enzyme were added to the whole stillage obtained from a dry grind, corn ethanol process. The alpha amylase was added into the whole stillage for 1 hour or 4 hours. Alpha amylase of the invention was added at a 1.0× loading as noted in Example 4. The whole stillage is centrifuged to produce thin stillage. Through a series of evaporations and centrifugations, the oil was extracted from 30 ml of thin stillage. The thin stillage was washed three times with 15 ml each of hexane. The hexane was evaporated and the resulting oil residue weighed.

What is claimed is:

1. A method for increasing the oil yield in an ethanol production process comprising: adding a liquid enzyme formulation having an alpha-amylase titrated from a pH of 8.0 to 10.5, a buffering agent, a stabilizer, and a preservative wherein the pH of the enzyme formulation is about pH 6.0-8.0 to a beer, a distillation, a whole stillage, a centrifugation, a thin stillage, an evaporator, a syrup, or an oil recovery unit, and wherein the alpha-amylase comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to one of the amino acid sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

2. The liquid enzyme formulation of claim 1, wherein the pH of the liquid enzyme formulation is about pH 6.3-6.7.

3. The liquid enzyme formulation of claim 1, wherein the stabilizer comprises sucrose, sorbitol, mannitol, glycerol, trehalose, sodium chloride, sodium sulfate, or any combination thereof.

4. The liquid enzyme formulation of claim 1, wherein the buffering agent comprises: sodium citrate, potassium citrate, citric acid, sodium acetate, acetic acid, sodium phosphate, potassium phosphate, or any combination thereof.

5. The liquid enzyme formulation of claim 1, wherein the alpha-amylase retains at least 90% of its activity at a temperature of 4-40° C.

6. The liquid enzyme formulation of claim 1, wherein the alpha-amylase retains at least 90% of its activity at a temperature of 25-30° C.

7. The liquid enzyme formulation of claim 1, wherein the alpha-amylase retains at least 90% of its activity for 1 year.

8. The liquid enzyme formulation of claim 1, wherein the alpha-amylase has a shelf life of at least 1 year.

9. The liquid enzyme formulation of claim 8, wherein the alpha-amylase has a shelf life of at least 1 year at 25° C.

10. The liquid enzyme formulation of claim 1, wherein the preservative comprises: potassium sorbate, sodium sorbate, sorbic acid, sodium benzoate, benzoic acid, methyl paraben, calcium propionate, sodium propionate, ammonium propionate, propionic acid, or any combination thereof.

11. The liquid enzyme formulation of claim 1, further comprising at least two preservatives.

12. The liquid enzyme formulation of claim 1, further comprising a second enzyme.

13. The liquid enzyme formulation of claim 12, wherein the second enzyme is selected from the group consisting of a second alpha-amylase, a beta-amylase, a glucoamylase, a protease, a phytase, a pullulanase, a cellulase, a cellobiohydrolase, a beta-glucosidase, an endoglucanase, a mannanase, a xylanase, a lipase, a phospholipase, and any combination thereof.

14. The method of claim 1, wherein a liquid enzyme formulation having at least one enzyme is added to a first stillage composition to form a second stillage composition, wherein the one or more alpha amylase enzymes are added to the first stillage composition in an amount from 0.001 to 0.01 grams/100 grams of solids of the first stillage composition; and obtaining oil from the second stillage composition.

15. The method of claim 14, wherein the first stillage composition comprises whole stillage, thin stillage, wet cake and/or syrup.

* * * * *